United States Patent
Zobel

(10) Patent No.: US 10,054,772 B1
(45) Date of Patent: Aug. 21, 2018

(54) DIFFRACTION LIMITED ENDOSCOPE

(71) Applicant: Integrated Medical Systems International, Inc., Birmingham, AL (US)

(72) Inventor: Jurgen Zobel, Pembroke Pines, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 0 days.

(21) Appl. No.: 15/624,294

(22) Filed: Jun. 15, 2017

Related U.S. Application Data

(63) Continuation-in-part of application No. 14/163,430, filed on Jan. 24, 2014, now abandoned.

(60) Provisional application No. 61/756,374, filed on Jan. 24, 2013.

(51) Int. Cl.
*G02B 13/00* (2006.01)
*A61B 1/00* (2006.01)
*G02B 27/00* (2006.01)

(52) U.S. Cl.
CPC ...... *G02B 13/0095* (2013.01); *A61B 1/00163* (2013.01); *G02B 27/0025* (2013.01)

(58) Field of Classification Search
CPC ............ G02B 13/0095; G02B 27/0025; A61B 1/0011; A61B 1/00163
USPC .......................................... 359/435, 735, 689
See application file for complete search history.

(56) References Cited

U.S. PATENT DOCUMENTS

| 3,994,557 | A | * | 11/1976 | Hopkins | ................ | A61B 1/307 |
| | | | | | | 359/374 |
| 5,327,283 | A | * | 7/1994 | Zobel | .................. | G02B 23/243 |
| | | | | | | 359/434 |
| 6,490,085 | B1 | * | 12/2002 | Zobel | ................ | G02B 23/2446 |
| | | | | | | 359/435 |

OTHER PUBLICATIONS

Lee; "The Hartmann Formula for the Dispersion of Glass;" Transactions of the Optical Society, vol. 28, Issue 3, pp. 161-167 (1926).*
Hartmann; "A Simple Interpolation Formula for the Prismatic Spectrum;" Astrophysical Journal, vol. 8, p. 218 (1898).*

* cited by examiner

*Primary Examiner* — Jordan Schwartz
*Assistant Examiner* — George G King
(74) *Attorney, Agent, or Firm* — C. Brandon Browning; Maynard, Cooper & Gale, PC

(57) ABSTRACT

An optical system for endoscopes for which the corrections of the geometrical optical aberrations for multiple wavelengths meet the diffraction limit of the optical system. The optical system is categorized by lens groups. The glass selection for each of these lens groups uses the Hartmann Dispersion Formula. For the glasses in each lens group, limited ranges for the $\lambda_o$ value of the Hartmann Dispersion Formula are set. These ranges are set based on the contribution of the individual lens groups to the overall chromatic aberrations.

29 Claims, 23 Drawing Sheets

| Glass Type | $n_c$ | $n_d$ | $n_F$ |
|---|---|---|---|
| F2 | 1.615032 | 1.620040 | 1.632081 |
| F2HT | 1.615032 | 1.620040 | 1.632081 |
| F5 | 1.598745 | 1.603420 | 1.614612 |
| K10 | 1.498672 | 1.501371 | 1.507560 |
| K7 | 1.508541 | 1.511121 | 1.517002 |
| KZFS12 | 1.690329 | 1.696000 | 1.709508 |
| KZFSN5 | 1.649201 | 1.654117 | 1.665707 |
| LAFN7 | 1.743194 | 1.749502 | 1.764639 |
| LF5 | 1.577229 | 1.581440 | 1.591462 |
| LLF1 | 1.544566 | 1.548140 | 1.556547 |
| N-BAF10 | 1.665778 | 1.670030 | 1.680000 |
| N-BAF4 | 1.601566 | 1.605683 | 1.615419 |
| N-BAF51 | 1.647921 | 1.652240 | 1.662428 |
| N-BAF52 | 1.604732 | 1.608631 | 1.617794 |
| N-BAK1 | 1.569487 | 1.572500 | 1.579435 |
| N-BAK2 | 1.537209 | 1.539960 | 1.546252 |
| N-BAK4 | 1.565749 | 1.568827 | 1.575911 |
| N-BALF4 | 1.576311 | 1.579559 | 1.587071 |
| N-BALF5 | 1.544303 | 1.547390 | 1.554509 |
| N-BASF2 | 1.659055 | 1.664460 | 1.677512 |
| N-BASF64 | 1.698716 | 1.704000 | 1.716592 |
| N-BK10 | 1.495521 | 1.497821 | 1.502957 |
| N-BK7 | 1.514322 | 1.516800 | 1.522376 |
| N-BK7HT | 1.514322 | 1.516800 | 1.522376 |
| N-F2 | 1.615058 | 1.620053 | 1.632078 |
| N-FK5 | 1.485345 | 1.487490 | 1.492269 |
| N-FK51A | 1.484797 | 1.486561 | 1.490557 |
| N-K5 | 1.519815 | 1.522489 | 1.528599 |
| N-KF9 | 1.520400 | 1.523459 | 1.530556 |
| N-KZFS11 | 1.633238 | 1.637750 | 1.648275 |
| N-KZFS2 | 1.555195 | 1.558360 | 1.565533 |
| N-KZFS4 | 1.609217 | 1.613360 | 1.623002 |
| N-KZFS5 | 1.649223 | 1.654120 | 1.665700 |
| N-KZFS8 | 1.714365 | 1.720470 | 1.735128 |
| N-LAF2 | 1.739030 | 1.743972 | 1.755618 |
| N-LAF21 | 1.783007 | 1.788000 | 1.799600 |
| N-LAF33 | 1.780494 | 1.785825 | 1.798333 |
| N-LAF34 | 1.767802 | 1.772500 | 1.783370 |
| N-LAF35 | 1.738761 | 1.743300 | 1.753807 |
| N-LAF36 | 1.793897 | 1.799518 | 1.812768 |
| N-LAF7 | 1.743198 | 1.749500 | 1.764723 |
| N-LAK10 | 1.715725 | 1.720028 | 1.729949 |
| N-LAK12 | 1.674186 | 1.677900 | 1.686467 |

FIG. 13

| | | | |
|---|---|---|---|
| N-LAK14 | 1.692966 | 1.696800 | 1.705541 |
| N-LAK21 | 1.637242 | 1.640495 | 1.647899 |
| N-LAK22 | 1.647599 | 1.651130 | 1.659249 |
| N-LAK33A | 1.749557 | 1.753930 | 1.763980 |
| N-LAK33B | 1.750623 | 1.755000 | 1.765059 |
| N-LAK34 | 1.725090 | 1.729160 | 1.738469 |
| N-LAK7 | 1.648210 | 1.651600 | 1.659345 |
| N-LAK8 | 1.708974 | 1.713003 | 1.722219 |
| N-LAK9 | 1.687159 | 1.691002 | 1.699789 |
| N-LASF31A | 1.876561 | 1.883000 | 1.898225 |
| N-LASF40 | 1.827451 | 1.834044 | 1.849814 |
| N-LASF41 | 1.829228 | 1.835010 | 1.848589 |
| N-LASF43 | 1.800202 | 1.806100 | 1.820051 |
| N-LASF44 | 1.799008 | 1.804200 | 1.816303 |
| N-LASF45 | 1.794358 | 1.801070 | 1.817263 |
| N-LASF45HT | 1.794358 | 1.801070 | 1.817263 |
| N-LASF46A | 1.895258 | 1.903660 | 1.924111 |
| N-LASF46B | 1.895262 | 1.903660 | 1.924114 |
| N-LASF9 | 1.842554 | 1.850249 | 1.868984 |
| N-LASF9HT | 1.842554 | 1.850249 | 1.868984 |
| N-PK51 | 1.526463 | 1.528554 | 1.533329 |
| N-PK52A | 1.495139 | 1.497000 | 1.501229 |
| N-PSK3 | 1.549651 | 1.552322 | 1.558355 |
| N-PSK53A | 1.615032 | 1.618000 | 1.624782 |
| N-SF1 | 1.710349 | 1.717360 | 1.734568 |
| N-SF10 | 1.720906 | 1.728277 | 1.746431 |
| N-SF11 | 1.775955 | 1.784720 | 1.806513 |
| N-SF14 | 1.753565 | 1.761820 | 1.782280 |
| N-SF15 | 1.692217 | 1.698920 | 1.715359 |
| N-SF2 | 1.642101 | 1.647690 | 1.661252 |
| N-SF4 | 1.747186 | 1.755131 | 1.774769 |
| N-SF5 | 1.666638 | 1.672707 | 1.687496 |
| N-SF57 | 1.836496 | 1.846660 | 1.872100 |
| N-SF57HT | 1.836496 | 1.846660 | 1.872100 |
| N-SF57HTultra | 1.836496 | 1.846660 | 1.872100 |
| N-SF6 | 1.796079 | 1.805180 | 1.827829 |
| N-SF66 | 1.910387 | 1.922860 | 1.954586 |
| N-SF6HT | 1.796079 | 1.805180 | 1.827829 |
| N-SF6HTultra | 1.796079 | 1.805180 | 1.827829 |
| N-SF8 | 1.682544 | 1.688936 | 1.704549 |
| N-SK11 | 1.561010 | 1.563840 | 1.570284 |
| N-SK14 | 1.600075 | 1.603110 | 1.610028 |
| N-SK16 | 1.617272 | 1.620410 | 1.627556 |
| N-SK2 | 1.604135 | 1.607381 | 1.614857 |

FIG. 13 (Cont.)

| | | | |
|---|---|---|---|
| N-SK2HT | 1.604135 | 1.607381 | 1.614857 |
| N-SK4 | 1.609542 | 1.612718 | 1.619992 |
| N-SK5 | 1.586193 | 1.589130 | 1.595809 |
| N-SSK2 | 1.618771 | 1.622294 | 1.630452 |
| N-SSK5 | 1.654554 | 1.658440 | 1.667494 |
| N-SSK8 | 1.614011 | 1.617728 | 1.626408 |
| N-ZK7 | 1.505919 | 1.508469 | 1.514229 |
| P-LAF37 | 1.750537 | 1.755500 | 1.767083 |
| P-LAK35 | 1.689553 | 1.693500 | 1.702589 |
| P-LASF47 | 1.800235 | 1.806100 | 1.819944 |
| P-LASF50 | 1.802657 | 1.808600 | 1.822642 |
| P-LASF51 | 1.804111 | 1.810000 | 1.823903 |
| P-PK53 | 1.524474 | 1.526900 | 1.532430 |
| P-SF67 | 1.894798 | 1.906800 | 1.937172 |
| P-SF68 | 1.991715 | 2.005200 | 2.039582 |
| P-SF69 | 1.715350 | 1.722500 | 1.740068 |
| P-SF8 | 1.682525 | 1.688930 | 1.704571 |
| P-SK57 | 1.583993 | 1.587000 | 1.593842 |
| P-SK58A | 1.586180 | 1.589130 | 1.595814 |
| P-SK60 | 1.607136 | 1.610350 | 1.617678 |
| SF1 | 1.710313 | 1.717360 | 1.734620 |
| SF10 | 1.720848 | 1.728250 | 1.746481 |
| SF2 | 1.642096 | 1.647689 | 1.661231 |
| SF4 | 1.747298 | 1.755201 | 1.774681 |
| SF5 | 1.666610 | 1.672697 | 1.687495 |
| SF56A | 1.776053 | 1.784701 | 1.806145 |
| SF57 | 1.836504 | 1.846663 | 1.872040 |
| SF57HHT | 1.836504 | 1.846663 | 1.872040 |
| SF6 | 1.796092 | 1.805182 | 1.827752 |
| SF6HT | 1.796092 | 1.805182 | 1.827752 |
| LITHOSIL-Q | 1.456342 | 1.458438 | 1.463101 |
| SF57HTultra | 1.836504 | 1.846663 | 1.872040 |
| BAL15Y | 1.553826 | 1.556711 | 1.563313 |
| BAL35Y | 1.586190 | 1.589130 | 1.595811 |
| BSL7Y | 1.513855 | 1.516330 | 1.521892 |
| BSM51Y | 1.600073 | 1.603109 | 1.610017 |
| LAH80 | 1.876474 | 1.885000 | 1.905814 |
| L-BAL35 | 1.586178 | 1.589130 | 1.595812 |
| L-BAL42 | 1.580134 | 1.583126 | 1.589954 |
| L-BBH1 | 2.083900 | 2.102050 | 2.149610 |
| L-BSL7 | 1.513846 | 1.516330 | 1.521905 |
| L-LAH53 | 1.800238 | 1.806098 | 1.819956 |
| L-LAH81 | 1.800179 | 1.806100 | 1.820131 |
| L-LAH83 | 1.857672 | 1.864000 | 1.878964 |

FIG. 13 (Cont.)

|         |          |          |          |
|---------|----------|----------|----------|
| L-LAH84 | 1.802660 | 1.808600 | 1.822665 |
| L-LAH85 | 1.847717 | 1.854000 | 1.868859 |
| L-LAH85V | 1.847721 | 1.854000 | 1.868871 |
| L-LAH86 | 1.894221 | 1.902699 | 1.923335 |
| L-LAH87 | 1.765425 | 1.770300 | 1.781676 |
| L-LAL12 | 1.674150 | 1.677900 | 1.686500 |
| L-LAL13 | 1.689551 | 1.693500 | 1.702590 |
| L-LAM60 | 1.738655 | 1.743198 | 1.753731 |
| L-LAM69 | 1.725416 | 1.730770 | 1.743456 |
| L-LAM72 | 1.728579 | 1.733099 | 1.743572 |
| L-NBH54 | 1.891671 | 1.902000 | 1.927605 |
| L-PHL1  | 1.561735 | 1.564550 | 1.571018 |
| L-PHL2  | 1.556083 | 1.558800 | 1.565015 |
| L-TIH53 | 1.836480 | 1.846660 | 1.872093 |
| L-TIM28 | 1.682490 | 1.688931 | 1.704658 |
| PBH56   | 1.831573 | 1.841390 | 1.865832 |
| PBL25Y  | 1.577217 | 1.581439 | 1.591479 |
| PBL26Y  | 1.563391 | 1.567322 | 1.576629 |
| PBL6Y   | 1.528459 | 1.531717 | 1.539320 |
| PBM18Y  | 1.590974 | 1.595509 | 1.606336 |
| PBM2Y   | 1.615019 | 1.620041 | 1.632114 |
| PBM8Y   | 1.591030 | 1.595509 | 1.606198 |
| S-BAH10 | 1.665788 | 1.670029 | 1.679974 |
| S-BAH11 | 1.662589 | 1.666718 | 1.676385 |
| S-BAH27 | 1.696503 | 1.701536 | 1.713514 |
| S-BAH28 | 1.717816 | 1.723420 | 1.736875 |
| S-BAH32 | 1.664949 | 1.669979 | 1.682010 |
| S-BAL11 | 1.569489 | 1.572501 | 1.579404 |
| S-BAL12 | 1.537194 | 1.539956 | 1.546275 |
| S-BAL14 | 1.565775 | 1.568832 | 1.575867 |
| S-BAL2  | 1.567616 | 1.570989 | 1.578856 |
| S-BAL22 | 1.565965 | 1.568729 | 1.574978 |
| S-BAL3  | 1.568105 | 1.571351 | 1.578894 |
| S-BAL35 | 1.586187 | 1.589130 | 1.595824 |
| S-BAL41 | 1.561001 | 1.563839 | 1.570295 |
| S-BAL42 | 1.580139 | 1.583126 | 1.589960 |
| S-BAM12 | 1.635057 | 1.639300 | 1.649304 |
| S-BAM3  | 1.578929 | 1.582673 | 1.591481 |
| S-BAM4  | 1.601507 | 1.605620 | 1.615364 |
| S-BSL7  | 1.513855 | 1.516330 | 1.521905 |
| S-BSM10 | 1.619489 | 1.622799 | 1.630405 |
| S-BSM14 | 1.600078 | 1.603112 | 1.610024 |
| S-BSM15 | 1.619739 | 1.622992 | 1.630450 |
| S-BSM16 | 1.617275 | 1.620411 | 1.627566 |

FIG. 13 (Cont.)

| | | | |
|---|---|---|---|
| S-BSM18 | 1.635051 | 1.638539 | 1.646581 |
| S-BSM2 | 1.604144 | 1.607379 | 1.614834 |
| S-BSM21 | 1.613751 | 1.617195 | 1.625167 |
| S-BSM22 | 1.618770 | 1.622296 | 1.630474 |
| S-BSM25 | 1.654553 | 1.658441 | 1.667494 |
| S-BSM28 | 1.614005 | 1.617722 | 1.626405 |
| S-BSM4 | 1.609547 | 1.612716 | 1.619982 |
| S-BSM71 | 1.644815 | 1.648498 | 1.657046 |
| S-BSM81 | 1.636728 | 1.639999 | 1.647381 |
| S-BSM9 | 1.610673 | 1.614047 | 1.621839 |
| S-FPL51 | 1.495136 | 1.496999 | 1.501231 |
| S-FPL51Y | 1.495133 | 1.497003 | 1.501258 |
| S-FPL53 | 1.437333 | 1.438750 | 1.441954 |
| S-FPM2 | 1.592555 | 1.595220 | 1.601342 |
| S-FSL5 | 1.485344 | 1.487490 | 1.492285 |
| S-FSL5Y | 1.485346 | 1.487490 | 1.492275 |
| S-FTL10 | 1.498685 | 1.501372 | 1.507571 |
| S-FTM16 | 1.587794 | 1.592701 | 1.604580 |
| S-LAH51 | 1.780584 | 1.785896 | 1.798364 |
| S-LAH52 | 1.793879 | 1.799516 | 1.812814 |
| S-LAH53 | 1.800248 | 1.806098 | 1.819944 |
| S-LAH55V | 1.828981 | 1.834807 | 1.848520 |
| S-LAH58 | 1.876560 | 1.882997 | 1.898220 |
| S-LAH59 | 1.810749 | 1.816000 | 1.828252 |
| S-LAH60 | 1.827376 | 1.834000 | 1.849819 |
| S-LAH63 | 1.798375 | 1.804398 | 1.818696 |
| S-LAH64 | 1.782998 | 1.788001 | 1.799634 |
| S-LAH65 | 1.798815 | 1.804000 | 1.816079 |
| S-LAH65V | 1.798816 | 1.803999 | 1.816076 |
| S-LAH66 | 1.767798 | 1.772499 | 1.783373 |
| S-LAH71 | 1.842586 | 1.850259 | 1.868934 |
| S-LAH79 | 1.993011 | 2.003300 | 2.028496 |
| S-LAL10 | 1.715670 | 1.719995 | 1.730004 |
| S-LAL12 | 1.674188 | 1.677900 | 1.686438 |
| S-LAL13 | 1.689548 | 1.693501 | 1.702582 |
| S-LAL14 | 1.692974 | 1.696797 | 1.705521 |
| S-LAL18 | 1.725101 | 1.729157 | 1.738436 |
| S-LAL54 | 1.647485 | 1.650996 | 1.659076 |
| S-LAL56 | 1.673880 | 1.677898 | 1.687245 |
| S-LAL58 | 1.689393 | 1.693495 | 1.703042 |
| S-LAL59 | 1.729679 | 1.733997 | 1.743939 |
| S-LAL61 | 1.736727 | 1.740999 | 1.750804 |
| S-LAL7 | 1.648207 | 1.651597 | 1.659335 |
| S-LAL8 | 1.708974 | 1.712995 | 1.722210 |

FIG. 13 (Cont.)

| | | | |
|---|---|---|---|
| S-LAL9 | 1.687169 | 1.691002 | 1.699774 |
| S-LAM2 | 1.739048 | 1.743997 | 1.755660 |
| S-LAM3 | 1.712528 | 1.717004 | 1.727488 |
| S-LAM51 | 1.695636 | 1.699998 | 1.710195 |
| S-LAM52 | 1.715105 | 1.720000 | 1.731585 |
| S-LAM54 | 1.752234 | 1.756998 | 1.768063 |
| S-LAM55 | 1.756385 | 1.762001 | 1.775388 |
| S-LAM58 | 1.714919 | 1.720000 | 1.732071 |
| S-LAM59 | 1.692696 | 1.697002 | 1.707062 |
| S-LAM60 | 1.738653 | 1.743198 | 1.753716 |
| S-LAM61 | 1.715329 | 1.720002 | 1.730973 |
| S-LAM66 | 1.794275 | 1.800999 | 1.817182 |
| S-LAM7 | 1.743275 | 1.749497 | 1.764517 |
| S-NBH5 | 1.649225 | 1.654115 | 1.665708 |
| S-NBH51 | 1.743259 | 1.749504 | 1.764472 |
| S-NBH52 | 1.667780 | 1.672999 | 1.685421 |
| S-NBH53 | 1.731309 | 1.737999 | 1.754184 |
| S-NBH55 | 1.792237 | 1.799999 | 1.819042 |
| S-NBH8 | 1.714365 | 1.720467 | 1.735123 |
| S-NBM51 | 1.609248 | 1.613397 | 1.623105 |
| S-NPH1 | 1.798009 | 1.808095 | 1.833513 |
| S-NPH2 | 1.909158 | 1.922860 | 1.957994 |
| S-NPH3 | 1.943760 | 1.959060 | 1.998654 |
| S-NPH53 | 1.836536 | 1.846660 | 1.871985 |
| S-NSL3 | 1.515556 | 1.518229 | 1.524354 |
| S-NSL36 | 1.514444 | 1.517417 | 1.524313 |
| S-NSL5 | 1.519834 | 1.522494 | 1.528566 |
| S-PHM52 | 1.615036 | 1.618000 | 1.624794 |
| S-PHM53 | 1.600189 | 1.603001 | 1.609403 |
| S-TIH1 | 1.710332 | 1.717362 | 1.734634 |
| S-TIH10 | 1.720864 | 1.728250 | 1.746452 |
| S-TIH11 | 1.775964 | 1.784723 | 1.806518 |
| S-TIH13 | 1.733088 | 1.740769 | 1.759745 |
| S-TIH14 | 1.753567 | 1.761821 | 1.782296 |
| S-TIH18 | 1.714371 | 1.721507 | 1.739053 |
| S-TIH20 | 1.699084 | 1.705850 | 1.722422 |
| S-TIH23 | 1.776125 | 1.784696 | 1.805971 |
| S-TIH3 | 1.732453 | 1.739998 | 1.758605 |
| S-TIH4 | 1.747295 | 1.755199 | 1.774745 |
| S-TIH53 | 1.836488 | 1.846660 | 1.872095 |
| S-TIH6 | 1.796106 | 1.805181 | 1.827774 |
| S-TIL1 | 1.544572 | 1.548141 | 1.556544 |
| S-TIL2 | 1.537297 | 1.540720 | 1.548746 |
| S-TIL25 | 1.577216 | 1.581439 | 1.591485 |

FIG. 13 (Cont.)

| | | | |
|---|---|---|---|
| S-TIL26 | 1.563386 | 1.567322 | 1.576636 |
| S-TIL27 | 1.570902 | 1.575006 | 1.584756 |
| S-TIL6 | 1.528456 | 1.531717 | 1.539343 |
| S-TIM1 | 1.620743 | 1.625882 | 1.638275 |
| S-TIM2 | 1.615024 | 1.620041 | 1.632123 |
| S-TIM22 | 1.642096 | 1.647689 | 1.661262 |
| S-TIM25 | 1.666607 | 1.672700 | 1.687564 |
| S-TIM27 | 1.634375 | 1.639799 | 1.652938 |
| S-TIM28 | 1.682495 | 1.688931 | 1.704665 |
| S-TIM3 | 1.608062 | 1.612929 | 1.624626 |
| S-TIM35 | 1.692224 | 1.698947 | 1.715424 |
| S-TIM39 | 1.660925 | 1.666800 | 1.681097 |
| S-TIM5 | 1.598748 | 1.603420 | 1.614616 |
| S-TIM8 | 1.591030 | 1.595509 | 1.606205 |
| S-YGH51 | 1.750624 | 1.754998 | 1.765054 |

Hartmann Formula: $\quad n(\lambda) := n_0 + \dfrac{K}{\lambda - \lambda_0}$ $\lambda_r := 657.3711 \qquad \lambda_y := 588.9167 \qquad \lambda_b := 485.5041$ $n_r$, $n_y$ and $n_b$ given as numbers from Glass Manaufacturer Catalogs "I" $\quad n_r := n_0 + \dfrac{K}{\lambda_r - \lambda_0}$ "II" $\quad n_y := n_0 + \dfrac{K}{\lambda_y - \lambda_0}$ "III" $\quad n_b := n_0 + \dfrac{K}{\lambda_b - \lambda_0}$ Subtract equation II - I and II - II I' $\quad n_y - n_r = \dfrac{K}{\lambda_y - \lambda_0} - \dfrac{K}{\lambda_b - \lambda_0}$ II' $\quad n_b - n_y = \dfrac{K}{\lambda_b - \lambda_0} - \dfrac{K}{\lambda_y - \lambda_0}$

FIG. 14 (cont.)

Or transformed I' and II'

$$\text{I'} \quad K = \frac{(n_y - n_r)(\lambda_y - \lambda_0)(\lambda_r - \lambda_0)}{\lambda_r - \lambda_y}$$

$$\text{II'} \quad K = \frac{(n_b - n_y)(\lambda_b - \lambda_0)(\lambda_y - \lambda_0)}{\lambda_y - \lambda_b}$$

Finally equation I' and II' can be combined to III''

$$\text{III'} \quad \frac{(n_y - n_r)(\lambda_y - \lambda_0)(\lambda_r - \lambda_0)}{\lambda_r - \lambda_y} = \frac{(n_b - n_y)(\lambda_b - \lambda_0)(\lambda_y - \lambda_0)}{\lambda_y - \lambda_b}$$

$$\text{III'} \quad (n_y - n_r)(\lambda_y - \lambda_0)(\lambda_r - \lambda_0)(\lambda_y - \lambda_b) = (n_b - n_y)(\lambda_b - \lambda_0)(\lambda_y - \lambda_0)(\lambda_r - \lambda_y)$$

Divide both sides by $\lambda_y - \lambda_0$ unequal 0

$$\text{III'} \quad (n_y - n_r)(\lambda_r - \lambda_0)(\lambda_y - \lambda_b) = (n_b - n_y)(\lambda_b - \lambda_0)(\lambda_r - \lambda_y)$$

$$\text{III'} \quad (n_y - n_r)(\lambda_r - \lambda_0)(\lambda_y - \lambda_b) - (n_b - n_y)(\lambda_b - \lambda_0)(\lambda_r - \lambda_y) = 0$$

finally results in $$\lambda_0 := \frac{(\lambda_r - \lambda_b) \times n_y \times \lambda_y + (\lambda_y - \lambda_r) \times n_b \times \lambda_b + (\lambda_b - \lambda_y) \times n_r \times \lambda_r}{(\lambda_r - \lambda_b) \times n_y + (\lambda_y - \lambda_r) \times n_b + (\lambda_b - \lambda_y) \times n_r}$$

$$n_0 := \frac{(\lambda_r - \lambda_0) \times n_r - (\lambda_b - \lambda_0) \times n_b}{(\lambda_r - \lambda_b)}$$

$$K := (n_y - n_0) \times (\lambda_y - \lambda_0)$$

FIG. 15

| Glass | $n_D$ | K | lamda₀ | Glass | $n_D$ | K | lamda₀ | Glass | $n_D$ | K | lamda₀ | Glass | $n_D$ | K | lamda₀ |
|---|---|---|---|---|---|---|---|---|---|---|---|---|---|---|---|
| LLF1 | 1.52437 | 9.23 | 199.3 | PBL25Y | 1.55387 | 10.47 | 207.6 | S-NBH53 | 1.69549 | 15.63 | 219.8 | S-TIH3 | 1.69345 | 16.53 | 232.4 |
| S-BAM3 | 1.55779 | 9.66 | 199.6 | S-TIL25 | 1.55389 | 10.46 | 208.0 | S-FTM16 | 1.56157 | 11.43 | 220.3 | S-TIH13 | 1.69352 | 16.72 | 233.6 |
| S-LAH55V | 1.79611 | 15.00 | 199.9 | S-NBH52 | 1.63896 | 12.91 | 208.2 | SF2 | 1.61221 | 13.03 | 220.4 | N-SF4 | 1.70629 | 17.27 | 233.9 |
| S-TIL1 | 1.52445 | 9.18 | 200.1 | LF5 | 1.55398 | 10.42 | 208.2 | S-TIM27 | 1.60542 | 12.61 | 220.7 | S-TIH4 | 1.70665 | 17.16 | 234.2 |
| N-LAF2 | 1.71121 | 12.67 | 200.8 | S-BAH27 | 1.66872 | 12.45 | 208.2 | N-SF2 | 1.61236 | 12.92 | 221.9 | N-SF14 | 1.71127 | 17.80 | 235.5 |
| S-LAM2 | 1.71120 | 12.68 | 200.9 | KZFS12 | 1.65907 | 13.99 | 208.8 | S-TIM22 | 1.61234 | 12.93 | 222.0 | L-NBH54 | 1.83877 | 22.25 | 235.7 |
| N-LAF36 | 1.76228 | 14.39 | 201.0 | N-BASF64 | 1.66963 | 13.00 | 209.2 | SF5 | 1.63432 | 13.99 | 223.1 | SF56A | 1.73179 | 18.61 | 235.9 |
| S-BAM12 | 1.61120 | 10.86 | 201.2 | S-LAM55 | 1.72548 | 13.81 | 209.4 | S-TIM39 | 1.62982 | 13.45 | 223.8 | S-TIH14 | 1.71135 | 17.74 | 236.1 |
| KZFSN5 | 1.62156 | 10.58 | 201.2 | PBM8Y | 1.56643 | 10.97 | 210.2 | S-LAH71 | 1.80197 | 17.56 | 223.9 | S-TIH23 | 1.73234 | 18.38 | 236.5 |
| N-BAF51 | 1.62366 | 11.03 | 201.6 | PBM18Y | 1.56609 | 11.09 | 210.5 | L-LAH86 | 1.84935 | 19.40 | 223.9 | SF6 | 1.74967 | 19.48 | 236.7 |
| S-LAH52 | 1.76223 | 14.39 | 201.7 | S-LAH60 | 1.79104 | 16.19 | 210.7 | N-LASF46A | 1.85080 | 19.22 | 223.9 | SF6HT | 1.74967 | 19.48 | 236.7 |
| P-LASF47 | 1.76733 | 14.94 | 202.1 | S-TIM8 | 1.56647 | 10.94 | 210.8 | N-LASF9 | 1.80184 | 17.60 | 224.1 | N-SF11 | 1.73130 | 18.70 | 237.5 |
| P-LASF51 | 1.77108 | 15.00 | 202.2 | S-BAH32 | 1.63744 | 12.23 | 211.8 | N-LASF9HT | 1.80184 | 17.60 | 224.1 | S-TIH11 | 1.73141 | 18.64 | 238.0 |
| P-LASF50 | 1.76939 | 15.08 | 202.9 | N-LASF40 | 1.79141 | 16.02 | 211.9 | N-LASF46B | 1.85087 | 19.18 | 224.3 | N-SF6 | 1.74978 | 19.36 | 238.0 |
| N-KZFS5 | 1.62184 | 12.40 | 203.4 | F5 | 1.57323 | 11.32 | 212.5 | N-SF5 | 1.63458 | 13.83 | 224.7 | N-SF6HT | 1.74978 | 19.36 | 238.0 |
| L-LAH85 | 1.81259 | 15.91 | 203.4 | S-TIM5 | 1.57329 | 11.28 | 213.2 | S-TIM25 | 1.63450 | 13.83 | 225.4 | N-SF6HTultra | 1.74978 | 19.36 | 238.0 |
| N-LASF31A | 1.84057 | 16.30 | 203.4 | S-NBH51 | 1.70924 | 15.07 | 213.3 | LAH80 | 1.83180 | 19.31 | 225.9 | S-TIH6 | 1.74998 | 19.28 | 238.3 |
| S-LAH53 | 1.76748 | 14.83 | 203.5 | LAFN7 | 1.70892 | 15.15 | 214.2 | L-TIM28 | 1.64860 | 14.58 | 226.0 | PBH56 | 1.78167 | 20.86 | 238.3 |
| S-LAH58 | 1.84058 | 16.29 | 203.5 | S-BAH28 | 1.68739 | 13.44 | 214.6 | P-SF8 | 1.64882 | 14.50 | 226.0 | SF57 | 1.78517 | 21.35 | 240.4 |
| N-BAF4 | 1.57856 | 10.42 | 203.5 | N-KZFS8 | 1.68123 | 14.63 | 214.6 | N-SF8 | 1.64894 | 14.45 | 226.3 | SF57HT | 1.78517 | 21.35 | 240.4 |
| L-LAH83 | 1.82231 | 16.01 | 203.6 | S-NBH8 | 1.68126 | 14.62 | 214.8 | S-TIM28 | 1.64871 | 14.51 | 226.8 | SF57HTultra | 1.78517 | 21.35 | 240.4 |
| N-LASF43 | 1.76724 | 14.92 | 203.6 | S-TIM3 | 1.58169 | 11.63 | 215.2 | S-LAH79 | 1.93915 | 23.07 | 227.9 | L-TIH53 | 1.78506 | 21.38 | 240.5 |
| S-TIL26 | 1.54142 | 9.94 | 204.0 | PBM2Y | 1.58781 | 12.00 | 215.3 | S-TIH20 | 1.66367 | 15.17 | 228.0 | S-TIH53 | 1.78518 | 21.31 | 241.0 |
| S-LAM52 | 1.68779 | 12.35 | 204.2 | F2 | 1.58791 | 11.95 | 215.5 | SF1 | 1.67345 | 15.78 | 228.1 | S-NPH53 | 1.78551 | 21.18 | 241.2 |
| S-LAH53 | 1.76761 | 14.76 | 204.2 | F2HT | 1.58791 | 11.95 | 215.5 | S-TIM35 | 1.65709 | 15.03 | 228.5 | N-SF57 | 1.78531 | 21.23 | 241.5 |
| PBL26Y | 1.54147 | 9.91 | 204.4 | S-LAM66 | 1.75793 | 15.99 | 216.2 | N-SF15 | 1.65721 | 14.96 | 228.8 | S-NF57HT | 1.78531 | 21.23 | 241.5 |
| L-LAH84 | 1.78955 | 14.96 | 204.5 | N-F2 | 1.58807 | 11.87 | 216.4 | S-NBH55 | 1.75174 | 17.30 | 229.1 | N-SF57HTult | 1.78531 | 21.23 | 241.5 |
| L-LAH85V | 1.81273 | 15.80 | 204.6 | S-TIM2 | 1.58795 | 11.90 | 216.7 | N-SF1 | 1.67380 | 15.60 | 229.4 | S-NPH1 | 1.74781 | 20.62 | 245.6 |
| S-BAM4 | 1.57860 | 10.34 | 204.9 | S-TIM1 | 1.59308 | 12.14 | 217.6 | S-TIH1 | 1.67375 | 15.59 | 230.1 | P-SF67 | 1.83547 | 24.22 | 247.9 |
| L-LAH81 | 1.76721 | 14.88 | 205.0 | N-LASF45 | 1.75825 | 15.83 | 217.9 | P-SF69 | 1.67815 | 15.85 | 230.1 | N-SF66 | 1.84926 | 24.78 | 250.8 |
| L-LAM69 | 1.69561 | 13.45 | 205.0 | N-LASF45HT | 1.75825 | 15.83 | 217.9 | S-TIH18 | 1.67730 | 15.78 | 230.6 | P-SF68 | 1.92589 | 26.60 | 252.2 |
| S-NBH5 | 1.62202 | 12.27 | 205.4 | S-LAM7 | 1.70983 | 14.65 | 218.3 | SF10 | 1.68249 | 16.29 | 231.5 | S-NPH2 | 1.84290 | 26.57 | 255.3 |
| S-LAH63 | 1.78497 | 15.03 | 205.4 | N-BASF2 | 1.63002 | 12.71 | 218.5 | N-SF10 | 1.68272 | 16.22 | 231.6 | S-NPH3 | 1.87086 | 28.87 | 260.2 |
| S-LAM58 | 1.66677 | 12.65 | 206.9 | N-LAF7 | 1.70938 | 14.79 | 218.8 | S-TIH10 | 1.68265 | 16.21 | 232.1 | L-BBH1 | 1.99913 | 33.03 | 266.6 |
| S-TIL27 | 1.54818 | 10.21 | 207.0 | N-LAF7 | 1.70939 | 14.79 | 218.9 | SF4 | 1.70641 | 17.34 | 232.1 | | | | |

FIG. 15 (cont)

| Surface | Radius | Thickness | Glass | Diameter | Glass Constants for Hartman's Dispersion Formula | | | range | Comment |
|---|---|---|---|---|---|---|---|---|---|
| | | | | | $n_0$ | K | $\lambda_0$ [nm] | | |
| 1 | 5.610035 | 0.9821785 | N-LASF31A | 5 | 1.84057 | 16.30 | 203.4 | $\lambda_0$ - values: [198.7 to 203.4] $\lambda_0$ - range: = 4.7 ≤ 25 | negative refractive power lens group |
| 2 | 55.27867 | 0.4402684 | N-BAF52 | 5 | 1.58267 | 10.09 | 198.7 | | |
| 3 | 1.465752 | 0.6839365 | | 2.447895 | | | | | |
| 4 | 9.876288 | 0.429658 | N-BAF52 | 3 | 1.58267 | 10.09 | 198.7 | | |
| 5 | 1.733287 | 0.5900101 | | 2.4 | | | | | |
| 6 | Infinity | 7.78883 | N-LASF31A | 5.2 | 1.84057 | 16.30 | 203.4 | | prism member |
| 7 | Infinity | 1.944562 | N-PK51 | 4.758291 | 1.51390 | 6.05 | 174.8 | $\lambda_0$ - values: [172.5 to 186.7] $\lambda_0$ - range: = 14.2 ≤ 15 | objective lens group |
| 8 | -4.775724 | 0.2966483 | | 6.5 | | | | | |
| 9 | -1361.692 | 1.198964 | S-PHM53 | 6.2 | 1.58321 | 8.21 | 172.6 | | |
| 10 | -9.589029 | 0.2925918 | | 6.2 | | | | | |
| 11 | 87.80483 | 0.9460274 | N-LAF35 | 5.8 | 1.71228 | 12.44 | 186.7 | | |
| 12 | 7.128672 | 2.001563 | N-PK51 | 5.8 | 1.51390 | 6.05 | 174.8 | | |
| 13 | -9.617602 | 1.006183 | | 5.8 | | | | | |
| 14 | 10.91222 | 1.542647 | N-PK51 | 5.5 | 1.51390 | 6.05 | 174.8 | | |
| 15 | -9.747481 | 0.5340627 | | 5.5 | | | | | |
| 16 | -5.548638 | 1.511419 | N-KZFS11 | 5 | 1.60733 | 12.00 | 193.0 | $\lambda_0$ - values: [168.0 to 193.0] $\lambda_0$ - range: = 25.0 ≤ 25 | field lens group |
| 17 | -18.33156 | 1.016858 | | 5.4 | | | | | |
| 18 | -5.353063 | 0.7437247 | N-KZFS11 | 4.6 | 1.60733 | 12.00 | 193.0 | | |
| 19 | 10.08158 | 0.8126996 | | 5.6 | | | | | |
| 20 | 20.77359 | 1.834862 | N-PK52A | 6 | 1.48386 | 5.47 | 171.0 | | |
| 21 | -4.724476 | 1.01468 | | 6 | | | | | |
| 22 | -6.295281 | 2.012324 | N-FK51A | 6 | 1.47403 | 5.26 | 168.0 | | |
| 23 | -6.510663 | 3.505173 | | 6.5 | | | | | |
| 24 | Infinity | 4.365983 | | 5.561252 | | | | | |

FIG. 16

| # | Radius | Thickness | Glass | | | | $\lambda_0$-values | Group | Side |
|---|---|---|---|---|---|---|---|---|---|
| 25 | 19.84135 | 48 | N-SK2HT | 1.58501 | 9.06 | 182.6 | | | field lens side |
| 26 | Infinity | 1 | N-LAK33A | 1.72364 | 12.33 | 180.5 | | | aperture side of second lens group |
| 27 | 20.58785 | 2.8 | N-PK51 | 1.51390 | 6.05 | 174.8 | | | |
| 28 | -14.47423 | 0.05 | | | | | $\lambda_0$-values: [174.8 to 182.6] $\lambda_0$-range: = 7.8 ≤ 15 | second lens group (symmetric relay assembly) | |
| 29 | Infinity | 0.05 | | | | 6.30127 | | | |
| 30 | 14.47423 | 2.8 | N-PK51 | 1.51390 | 6.05 | 174.8 | | | |
| 31 | -20.58785 | 1 | N-LAK33A | 1.72364 | 12.33 | 180.5 | | | |
| 32 | Infinity | 48 | N-SK2HT | 1.58501 | 9.06 | 182.6 | | | |
| 33 | -19.84135 | 4.365983 | | | | | | | field lens side |
| 34 | Infinity | 4.365983 | | | | 5.328578 | | | |
| 35 | 19.84135 | 48 | N-SK2HT | 1.58501 | 9.06 | 182.6 | | | aperture side of second lens group |
| 36 | Infinity | 1 | N-LAK33A | 1.72364 | 12.33 | 180.5 | | | |
| 37 | 20.58785 | 2.8 | N-PK51 | 1.51390 | 6.05 | 174.8 | | | |
| 38 | -14.47423 | 0.05 | | | | | $\lambda_0$-values: [174.8 to 182.6] $\lambda_0$-range: = 7.8 ≤ 15 | second lens group (symmetric relay assembly) | |
| STO | Infinity | 0.05 | | | | 6.3 | | | |
| 40 | 14.47423 | 2.8 | N-PK51 | 1.51390 | 6.05 | 174.8 | | | |
| 41 | -20.58785 | 1 | N-LAK33A | 1.72364 | 12.33 | 180.5 | | | |
| 42 | Infinity | 48 | N-SK2HT | 1.58501 | 9.06 | 182.6 | | | |
| 43 | -19.84135 | 4.365983 | | | | | | | field lens side |
| 44 | Infinity | 4.365983 | | | | 5.227237 | | | |
| 45 | 19.84135 | 48 | N-SK2HT | 1.58501 | 9.06 | 182.6 | | | aperture side of second lens group |
| 46 | Infinity | 1 | N-LAK33A | 1.72364 | 12.33 | 180.5 | | | |
| 47 | 20.58785 | 2.8 | N-PK51 | 1.51390 | 6.05 | 174.8 | | | |
| 48 | -14.47423 | 0.05 | | | | | $\lambda_0$-values: [174.8 to 182.6] $\lambda_0$-range: = 7.8 ≤ 15 | second lens group (symmetric relay assembly) | |
| 49 | Infinity | 0.05 | | | | 6.5 | | | |
| 50 | 14.47423 | 2.8 | N-PK51 | 1.51390 | 6.05 | 174.8 | | | |
| 51 | -20.58785 | 1 | N-LAK33A | 1.72364 | 12.33 | 180.5 | | | |
| 52 | Infinity | 48 | N-SK2HT | 1.58501 | 9.06 | 182.6 | | | |
| 53 | -19.84135 | 4.365983 | | | | | | | field lens side |
| 54 | Infinity | 16.93111 | | | | 5.127918 | | | |
| 55 | 27.57165 | 2 | S-PHM53 | 1.58321 | 8.21 | 172.6 | $\lambda_0$-values: [171.0 to 198.2] $\lambda_0$-range: = 27.2 ≤ 30 | third lens group (ocular lens assembly) | |
| 56 | -35.33198 | 0.5 | | | | | | | |
| 57 | Infinity | 1 | S-LAM61 | 1.68885 | 12.13 | 198.2 | | | |
| 58 | 9.616312 | 4 | N-PK52A | 1.48386 | 5.47 | 171.0 | | | |
| 59 | -13.34165 | 0 | | | | | | | |

FIG. 16 (cont)

DIFFRACTION LIMITED ENDOSCOPE

RELATED REFERENCES

This application claims priority to U.S. Non-provisional patent application Ser. No. 14/163,430, filed on Jan. 24, 2014, and titled "Diffraction Limited Endoscope," and U.S. Provisional Application No. 61/756,374, filed on Jan. 24, 2013, and titled, "Diffraction Limited Endoscope," the entire contents of which are incorporated herein by reference.

BACKGROUND OF INVENTION

Technical and medical endoscopes can be rigid endoscopes containing a lens system, flexible endoscopes containing a flexible image guiding bundle or video endoscopes. Rigid endoscopes are preferred by most physicians because of their optical quality and ease of handling.

Rigid endoscopes have a small diameter of a few millimeters but are often several hundreds of millimeters long. These endoscopes contain an outer tube and an inner tube. The space between the outer tube and inner tube is filled with illumination fibers which guide externally created light inside the cavities such as body cavities. Rigid endoscopes have inside the inner tube an optical system which relays an image created by an objective from the distal tip of the endoscope back to the proximal end of the endoscope. This image relayed to the proximal end can be observed by the operator's eye, or a video camera can capture the image.

First endoscopes with lens systems were simple designs with achromats as relay systems and oculars, plano-convex or bi-convex lenses as field lenses and objective lenses. The number of lenses was limited because the advantage of increasing the number of lenses is offset by the increase of reflections at the glass air surfaces. After the introduction of anti-reflection coatings the number of lenses and therewith the number of relay systems could be increased.

The brightness of modern endoscopes depends on the brightness of the relay system. This brightness is measured by the numerical aperture of the relay system. The numerical aperture is a dimensionless number that characterizes the range of angles over which the system can accept or emit light. By incorporating index of refraction in its definition, numerical aperture has the property that it is constant for a beam as it goes from one material to another provided there is no optical power at the interface.

Almost all endoscopic surgeries are done today using endoscopic cameras at the proximal end of the endoscopes. The physicians and their staff observe the endoscopic procedure on one or more monitors used in the operating room. Such endoscopic cameras have dramatically improved in the last years and exceed the former NTSC standard. Today, digital endoscopic cameras with high definition (HD) resolution are the norm in operating rooms.

Most optical designs of rigid endoscopes were developed twenty and more years ago, and the resolution of these endoscopes does not meet the resolution of modern HD cameras. The resolution of endoscopes is limited by either the diffraction limit represented by the so-called airy disk or by the spot size created by geometric optical aberrations. The airy disk refers to the bright spot in a diffraction pattern resulting from a uniformly-illuminated circular aperture. In an ideal corrected endoscope, the geometric optical aberrations will be optimized so much that the geometrical optical spot size meets roughly the airy disk representing the diffraction limit. Optical aberrations refer to departures of the performance of an optical system from the predictions of paraxial optics. Optical aberrations occur when light from one point of an object does not converge into, or does not diverge from, a single point after transmission through the system.

The diffraction limit of an endoscope depends on the numerical aperture of the relay system. The numerical aperture of the relay system is determined by the type of relay, free lens diameter and the length of the relay system. By manipulating these parameters the diffraction limit of the relay system can be reduced which results in a smaller airy disk and higher numerical aperture. However, the increase of the numerical aperture decreases the depth of field. So every optical system in an endoscope is a compromise between the depth of field and the size of the airy disk.

Endoscopes, like so-called needle scopes, with small outer diameter and therewith small lens diameter have a large diffraction limit. This is why the spot size of the geometrical optical aberrations of such endoscopes can also be larger. Conversely, endoscopes with a larger lens diameter have a lower diffraction limit. For such endoscopes today, the geometric optical aberrations are not corrected to match the diffraction limit.

In an optical design, basic monochromatic and chromatic aberrations of optical systems i.e., distortions in which there is a failure of a lens to focus all colors to the same convergence point, are minimized in a way that the spot size of the geometrical optical aberrations is minimized over the whole field. To achieve this not every component of the optical system needs to be fully optimized. As Ernst Abbe defined for the microscope, some components can be over corrected or under corrected for certain aberrations as long as the over corrected and under corrected aberrations from different components compensate in the whole instrument. To optimize the aberrations of endoscopes, the aberrations of the different components like the ocular, relay and objective systems must also compensate one another.

The five monochromatic aberrations are spherical aberration, coma, astigmatisms, field curvature and distortion. The two chromatic aberrations are axial color and lateral color. Coma, distortion and lateral color are caused by the asymmetry of an optical system or optical component. Correction of spherical aberrations and axial color are correlated. Axial color is the variation of the spherical aberrations for different colors of the visual spectrum.

The correction of aberrations in endoscopes can be shown by the classical Hopkins rod lens system which consists of a number of pairs of rod lenses where each pair is symmetrical to the center of the relay system. These symmetrical relay systems do not contribute to coma, distortion or lateral color of the whole optical system of the endoscope. The rod lenses in these relay system are simple achromatic systems which are designed to limit the effects of chromatic and spherical aberration. Astigmatism and field curvature are not fully corrected or in other terms under corrected. However, the achromatic system corrects the spherical aberrations and axial color. The relay system has the largest numerical aperture of all the components in the endoscope. Residual spherical aberrations and the variation of the spherical aberrations for different colors from the relay system will be dominant. Additionally, these aberrations are multiplied by the number of relay systems.

The ocular is usually a simple achromat. Used with a lower numerical aperture than the relay system, the ocular contributes also to the spherical aberrations and axial color but less than one single rod lens in the relay system. The ocular is unique in the endoscope system because the marker plate sitting in front of the ocular is the only element not seen through the whole optical system of the endoscope. The marker plate is a radial object located at the periphery of the object field of the ocular. Coma in the ocular design makes it impossible to focus on the marker plate. Lateral color causes a colored border of the marker plate. Therefore, the ocular has to be corrected for coma and lateral color for the edge of the field where the marker plate is located.

The objective system of the Hopkins design consists of four components or groups of components which have different functions and different influence on the total correction of the aberrations of the endoscope. At the distal tip is a lens or lens group with extreme high negative refractive power. This lens or lens group with high negative refractive power has an over corrected field curvature which compensates the remaining under corrected field curvature of all the other components of the optical system of the endoscope. A negative lens with extreme high refractive power creates also high distortion. Early Hopkins endoscopes did not correct this distortion. Later, designs reduced or corrected the distortion by introducing a cemented surface in the front lens group. The second group in the Hopkins objective is a prism or prism block which deflects the optical axis of the proximal part of the optical system of the endoscope laterally towards the object field.

On the proximal side of the prism comes first an objective lens or objective lens group followed by one or more field lenses. The objective lens or objective lens group and the field lenses ensure that the chief rays of the off axial object points cross inside the prism. Cemented surfaces within the objective and field lenses have extreme curvatures to create under corrected astigmatism to compensate the accumulated astigmatism of the relay system and ocular. The objective system also compensates the coma and lateral color. However, unlike the astigmatism there is no accumulated coma and lateral color from the relay system or ocular.

Axial and lateral color is normally calculated for three basic wavelengths of the visual spectrum. Achromatic systems correct the focus for two colors, typically close to the edges of the visual spectrum. This common focal length for the two colors for the edge of the spectrum is normally different for the focal length for the center wave length of the visible spectrum. The difference depends on the glass selection. Also, the spherical aberration of an achromatic system varies for different wave lengths. An endoscope corrected for axial and lateral color for three wave lengths still has aberrations for other wavelengths of the visual spectrum called secondary spectrum.

In view of the shortcomings of current endoscope optical systems, especially when used with HD cameras, there is a need for an optical system for endoscopes having low diffraction limit with a correction for the geometrical optical aberrations matching the diffraction limit of the optical system for more than the three basic wavelengths. Such a diffraction limited correction of the aberrations becomes more complicated with brighter optics and larger lens systems.

SUMMARY OF THE INVENTION

The present invention is directed to optical systems for endoscopes which have a low diffraction limit and require advanced optics and special glass selection to correct the geometrical optical aberrations for multiple wavelengths to meet the diffraction limit. The diffraction limit is set by the numerical aperture of the relay system and refers to the minimum angular separation of two sources that can be distinguished by an optical system, which depends on the wavelength of the light being observed and the diameter of the optical system.

To control the secondary spectrum and match the geometrical optical aberrations to the diffraction limit for more than the three basic colors in optical design, usually two more wavelengths at the periphery of the visual spectrum are added. The selection of glasses in the components of the endoscope is important. Those components with higher contribution to the spherical aberrations need a more careful selection of the glasses to reduce axial color.

The refractive index of an optical glass, which is a dimensionless number that describes how light propagates through a medium, is not constant. The refractive index of an optical glass varies as a function of the wavelength. This function is called the dispersion of a glass. There are several types of mathematical functions which approximate the refractive index as a function of the wavelength with high accuracy. Such a function is called a dispersion formula.

A simple formula describing the dispersion of optical glasses is the Hartmann Dispersion Formula, also referred to as the Cornu-Hartmann Formula. The formula relates the refraction index and wavelength. In the visual spectrum a good approximation is $n(\lambda)=n_o+K/(\lambda-\lambda_o)$, where $\lambda$ denotes the wavelength and $n_o$, $K$ and $\lambda_o$ are a set of constants varying for each individual glass type. The constant $n_o$ indicates if the glass in general has high or low refractive index. The constants $K$ and $\lambda_o$ describe the slope and bending of the curve of the dispersion.

Mathematical approximation of the chromatic variation of an optical system shows that glasses with similar values for $\lambda_o$ have a reduced secondary spectrum. Thus, the more sensitive the individual component is for spherical aberrations and therewith for axial color, the more important is it to select glasses with similar values for $\lambda_o$. To that end, the present invention separates the lenses and optical components in groups of optical elements, and based on the sensitivity to spherical aberrations and axial color, limits for the range of $\lambda_o$, i.e., the difference between the largest and smallest values of $\lambda_o$, are set accordingly for each group.

The most important group to achieve low spherical aberrations and low axial color is the relay system. In the present invention, symmetric relay systems are used to avoid coma, distortion and lateral color in the relay system. Symmetric relay systems are symmetric to the center of the relay system. This center represents the aperture stop of the relay systems and the aperture stop of the whole endoscope. In the following, only the contribution of one half of the symmetric relay system to the spherical aberration is considered. Both halves of the relay system contribute twice the aberrations. With multiple relays in the endoscope, the aberrations of one relay have to be multiplied with the number of relay systems.

In rod lens systems, a long glass cylinder is located between a lens or lens group on the image side and another lens or lens group at the aperture side. The cone of light coming from an object point is very small at the lens group on the image side. Therefore, the spherical aberrations of this lens or lens group are minimal. With low contributions to the spherical aberrations of the lens group at the image side, this group can be a single lens or even a plano convex lens cemented on the center rod. However, the $\lambda_o$ value of the glass selected needs to be close to the $\lambda_o$ values of the glasses on the aperture side.

The bundle of light coming from an object point opens at the lens or lens group on the aperture side and is equivalent to the free diameter of the lenses on this side. Therefore, the spherical aberrations of this lens or lens group have to be corrected to meet the diffraction limit of the endoscope. A single lens, meniscus or biconvex lens, as used in most conventional rods lens systems, is not sufficient. In the present invention, an achromatic lens group is used as a lens group at the aperture side. Because of the large height of the aperture rays at the aperture side of the relay system, the $\lambda_o$ value of the glasses in the lens group at the aperture side should be in a very close range of <=6 nm. However, the range for the $\lambda_o$ value of the glasses in the whole relay system can be in the range <=15 nm.

Achromats are commonly formed by two lenses called the flint lens mostly in form of a meniscus and a second lens called the crown lens mostly in the form of a biconvex lens. For systems with lower diffraction limit, the achromat in the relay system can be split and used with an air gap. Those types of achromats are called Gaussian achromats. To further enhance the correction of spherical aberrations, the biconvex part of the cemented or split achromat can have an aspherical surface. In another embodiment, the flint side of the cemented or split achromat can be cemented on the center rod. If the diffraction limit permits, the cemented achromat can have a plano surface on the flint lens, and the whole achromat can be cemented on the center rod.

The ocular of the present invention can be an achromat or an achromat with a single lens to reduce the curvatures on the ocular achromat. The glasses in the ocular are selected so that the glasses all have a similar value for $\lambda_o$. However, in the ocular the glass selection can be looser. A range of <=30 nm is acceptable.

For the monochromatic aberrations, the coma is corrected so that the ocular creates a sharp image of the marker plate without any colored borders. The proper glass selection regarding $\lambda_o$ and the curvatures of the ocular lenses can also be used to reduce the spherical aberration and the axial coma.

According to the present invention, the final balance of the aberrations is performed in the objective system. Like the classic Hopkins rod lens system, the objectives of the endoscopes of the present invention consist of four groups. At the distal tip is a lens or lens group with extreme high negative refractive power. The second group in the objective is a prism or prism block which deflects the optical axis. On the proximal side of the prism or prism group comes first a group of objective lenses followed by a group of field lenses.

The lens groups are complex in order to achieve an improved balance and correction of the aberrations to meet the diffraction limit set by the relay system. At first, the glass selection for each lens group in the objective has to consider how much the lens groups of the objective contribute to the axial or lateral color. For each group, a range for the $\lambda_o$ value of the glasses in this group is set. The range for the $\lambda_o$ value and the correction of the aberrations consider the relative height of the aperture and the field rays.

The lens group in the objective system with the largest relative heights of the aperture and field rays is the objective lens group. Therefore, the $\lambda_o$ value of the glasses in the objective lens group has to be in a range of <=15 nm. However, the relative heights of the aperture and field rays in the first lens group, the prism group and the field lens group are smaller than in the objective lens group. Consequently, the $\lambda_o$ value of the glasses in these groups can be in the range <=25 nm.

To correct the monochromatic aberrations together with the chromatic aberrations, each lens group in the objective system needs to contain three to five lenses as single lenses or cemented groups. These single lenses or cemented groups have to be centered and assembled in a mechanical housing. Based on mechanical and optical tolerances, it is necessary to align the lenses in each group against the mechanical axis, and the groups need to be aligned against one another.

It is desired to align the field lens group first and the objective lens group second. In a preferred embodiment, a shared mechanical housing holds the objective lens group and the field lens group. The mechanical housing has its smallest diameter in the middle of the housing separating the objective lens group and the field lens group. The field lens group can be assembled lens by lens from one side, and each lens is centered relative to the mechanical axis and fixed in the mechanical housing by glue or other means.

The objective lens group is then assembled in the same mechanical housing but from the other side of the mechanical housing. Again, each lens is centered under optical control to the mechanical axis and fixed in place by glue or other means. This way the two groups are assembled and centered against one another in the same long mechanical housing.

Preferably, the last lens in the objective group is a plano convex lens with the plano surface facing the prism. That way the prism can be assembled on the plano convex lens and glued in place. The lens group with extreme high negative refractive power will have centered lenses that are assembled together in a mechanical housing lens by lens. Each of the lenses are centered under optical control against the mechanical axis and fixed in place by glue or other means. The front lens group, with extreme high negative refractive power, is assembled in another mechanical housing that is aligned under optical control on top of the prism relative to the objective.

According to one aspect of the invention, there is provided an optical system for an endoscope including, from an object side of the optical system, an objective assembly including a first lens group for creating a first image, a symmetric relay assembly including a second lens group for transmitting the first image to a proximal end of the endoscope and an ocular lens assembly including a third lens group for observing the relayed first image, the first lens group including from the object side, a negative refractive power lens group, a prism member, an objective lens group and a field lens group. Each lens of the negative refractive power lens group and the prism member exhibits a $\lambda_o$ value within a first range of 25 nm or less, each lens of the objective lens group exhibits a $\lambda_o$ value within a second range of 15 nm or less, each lens of the field lens group exhibits a $\lambda_o$ value within a third range of 25 nm or less, each lens of the second lens group exhibits a $\lambda_o$ value within a fourth range of 15 nm or less, and each lens of the third lens group exhibits a $\lambda_o$ value within a fifth range of 30 nm or less, where the $\lambda_o$ value is expressed with the following formula:

$$n(\lambda)=n_o+K/(\lambda-\lambda_o)$$

where $\lambda$ denotes a wavelength and $n_o$, $K$ and $\lambda_o$ are a set of empirical constants varying for each lens glass type. The first range is the difference between a largest $\lambda o$ value and a smallest $\lambda o$ value represented by the lenses of the negative refractive power lens group and the prism member, the second range is the difference between a largest $\lambda o$ value and a smallest $\lambda o$ value represented by the lenses of the objective lens group, the third range is the difference between a largest $\lambda o$ value and a smallest $\lambda o$ value represented by the lenses of the field lens group, the fourth range is the difference between a largest $\lambda o$ value and a smallest $\lambda o$ value represented by the lenses of the second lens group, and the fifth range is the difference between a largest λo value and a smallest λo value represented by the lenses of the third lens group, the fourth range being smaller than the fifth range. In one embodiment, each of the first, second, third, fourth and fifth ranges is greater than 0. In another embodiment, one or more of the first, second, third, fourth and fifth ranges is greater than 0.

According to another aspect of the invention, there is provided an optical system for an endoscope including an objective assembly having a first lens group including a negative refractive power lens group, a prism member, an objective lens group and a field lens group, wherein each lens of the negative refractive power lens group and the prism group exhibits a $\lambda_o$ value within a first range of 25 nm or less, each lens of the objective lens group exhibits a $\lambda_o$ value within a second range of 15 nm or less, and each lens of the field lens group exhibits a $\lambda_o$ value within a third range of 25 nm or less, where the $\lambda_o$ value is expressed with the following formula:

$$n(\lambda)=n_o+K/(\lambda-\lambda_o)$$

where λ denotes a wavelength and $n_o$, K and $\lambda_o$ are a set of empirical constants varying for each lens glass type, the second range being smaller than the first range and the third range. The system further includes a relay assembly including a second lens group, and an ocular lens assembly including a third lens group. The negative refractive power lens group, the objective lens group and the field lens group each contains at least three lenses. The first range is the difference between a largest λo value and a smallest λo value represented by the lenses of the negative refractive power lens group and the prism member, the second range is the difference between a largest λo value and a smallest λo value represented by the lenses of the objective lens group, and the third range is the difference between a largest λo value and a smallest λo value represented by the lenses of the field lens group.

According to yet another aspect of the invention, there is provided a method of making an optical system for an endoscope including (i) selecting at least three lenses and a prism member that each exhibit a $\lambda_o$ value within a first range and arranging the at least three lenses into a negative refractive power lens assembly, the first range being the difference between a largest λo value and a smallest λo value represented by the at least three lenses of the negative refractive power lens assembly and the prism member, (ii) selecting at least three lenses that each exhibit a $\lambda_o$ value within a second range and arranging the at least three lenses into an objective lens assembly, the second range being the difference between a largest λo value and a smallest λo value represented by the at least three lenses of the objective lens assembly, (iii) selecting at least three lenses that each exhibit a $\lambda_o$ value within a third range and arranging the at least three lenses into a field lens assembly, the third range being the difference between a largest λo value and a smallest λo value represented by the at least three lenses of the field lens assembly, (iv) selecting a plurality of lenses that each exhibit a $\lambda_o$ value within a fourth range, wherein the fourth range is smaller than the first range, and arranging the plurality of lenses into a symmetric relay assembly, the fourth range being the difference between a largest λo value and a smallest λo value represented by the plurality of lenses of the relay assembly, (v) selecting a plurality of lenses that each exhibit a $\lambda_o$ value within a fifth range and arranging the plurality of lenses into an ocular lens assembly, the fifth range being the difference between a largest λo value and a smallest λo value represented by the plurality of lenses of the ocular lens assembly, and (vi) optically aligning the negative refractive power lens assembly, the prism member, the objective lens assembly, the field lens assembly, the symmetric relay assembly and the ocular lens assembly. The $\lambda_o$ value is expressed with the following formula:

$$n(\lambda)=n_o+K/(\lambda-\lambda_o)$$

where λ denotes a wavelength and $n_o$, K and $\lambda_o$ are a set of empirical constants varying for each lens glass type. Preferably, the first range is 25 nm or less, the second range is 15 nm or less, the third range is 25 nm or less, the fourth range is 15 nm or less, the fifth range is 30 nm or less. Thus, the fourth range is smaller than the third range and the fifth range.

BRIEF DESCRIPTION OF THE DRAWINGS

FIG. 1(*b*) depicts curves of five glass dispersion functions characterized by the Hartmann Dispersion Formula where only the $n_o$ values vary.

FIG. 1(*c*) depicts curves of five glass dispersion functions characterized by the Hartmann Dispersion Formula where only the K values vary.

FIG. 1(*d*) depicts curves of five glass dispersion functions characterized by the Hartmann Dispersion Formula where only the $\lambda_o$ values vary.

FIG. 1(*e*) depicts curves reflecting the variation of refractive power for different combinations of $\lambda_o$ values in an achromat.

FIG. 4(*b*) graphically depicts the variation of aberrations for a small range of $\lambda_o$ values of an optical system in accordance with the present invention.

FIG. 8(*b*) depicts another prior art objective system for Hopkins rod lens systems.

FIG. 8(*c*) depicts yet another prior art objective system for Hopkins rod lens systems.

FIG. 9(*b*) depicts a second objective system for a rod lens system in accordance with the present invention.

FIG. 9(*c*) depicts a third objective system for a rod lens system in accordance with the present invention.

FIG. 9(*d*) depicts a fourth objective system for a rod lens system in accordance with the present invention.

FIG. 9(*e*) depicts a fifth objective system for a rod lens system in accordance with the present invention.

FIG. 13 is a table depicting refractive indices for a number of glasses for three wavelengths.

FIG. 14 shows the derivation of the Hartmann formula for calculating the Hartman constants from three wavelengths.

FIG. 15 displays the Hartman constants for the glasses of FIG. 13.

FIG. 16 depicts an exemplary optical assembly of a scope in accordance with the present invention.

DETAILED DESCRIPTION OF THE DRAWINGS

The present invention is based upon the discovery that geometrical optical aberrations in endoscope optical assemblies can be corrected for multiple wavelengths by separating the lenses of the assemblies into groups of optical elements, and based on the sensitivity of the groups to spherical aberrations and axial color, setting limits for the ranges of λo for each group, i.e., the difference between the largest and smallest values of λo, where λo is an empirical constant for each lens glass type, as set forth in the Cornu-Hartmann Formula:

$$n(\lambda)=n_o+K/(\lambda-\lambda_o)$$

where λ denotes a wavelength and $n_o$, K and $\lambda_o$ are a set of empirical constants varying for each lens glass type.

This invention relates to an optical system for endoscopes for which the corrections of the geometrical optical aberrations for multiple wavelengths meet the diffraction limit of the optical system. The optical system is categorized by functional lens groups including an objective containing a front lens group, a prism block or glass block, an objective lens group and a field lens group, a relay lens group and an ocular lens group. The glass selection for these lens groups uses the Hartmann Dispersion Formula. For the glasses in each lens group, limited ranges for the $\lambda_o$ value of the Hartmann Dispersion Formula are set. These ranges are set based on the contribution of the individual lens groups to the overall chromatic aberrations. The relay system consists of a symmetric relay system with rod lenses where the lens group on the aperture side is an achromatic lens system with glasses different than the glass rod. This achromatic lens system can be split by an air gap, have aspheric surfaces, and the flint or whole achromat can be cemented to the glass rod. Each lens group consists of at least three to five lenses where, for each lens group, a limited range for the $\lambda_o$ value of the Hartmann Dispersion Formula is set. This limit is set based on the contributions of the lens group to the overall chromatic aberrations of the disclosed optical system. The front lens group is assembled in a metal cartridge, and the objective and field lens groups are assembled in a shared cartridge.

Figure 1A:
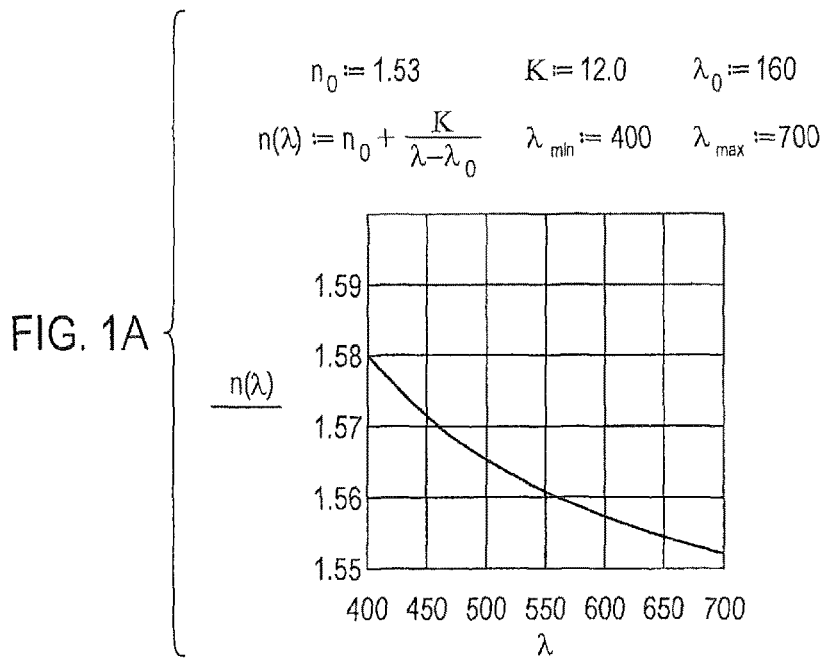
FIG. 1(*a*) depicts a curve of a glass dispersion function characterized by the Hartmann Dispersion Formula.
Figure 1B:
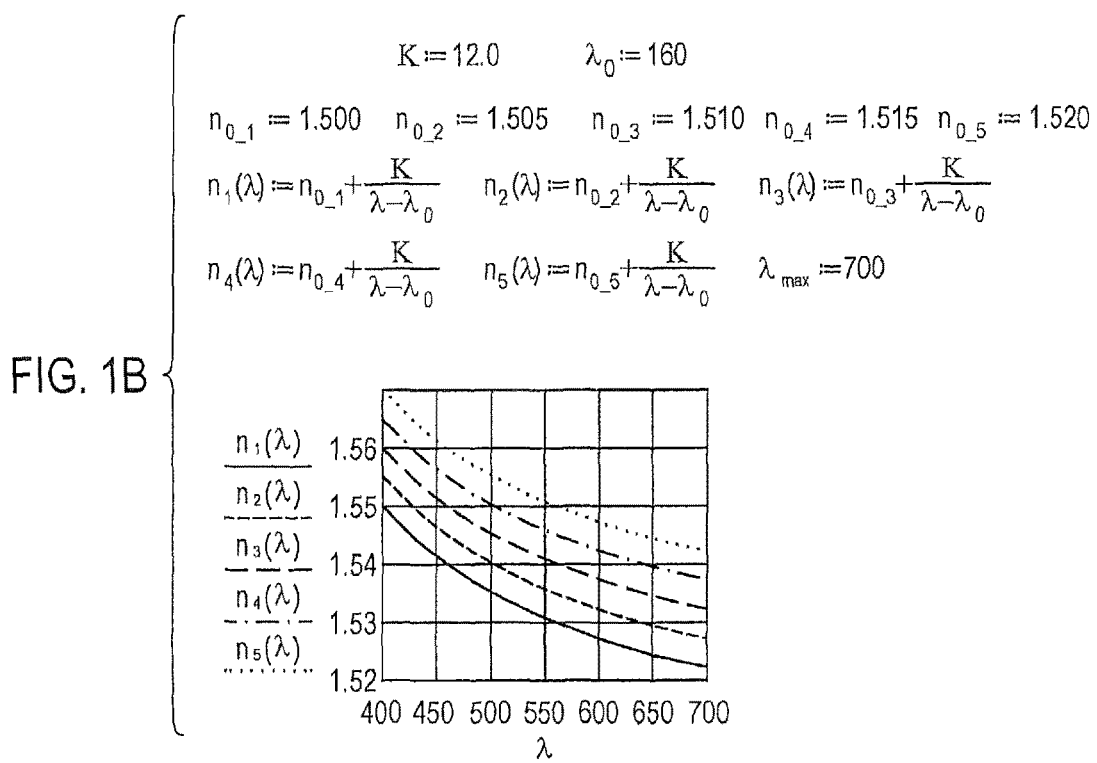
Figure 1C:
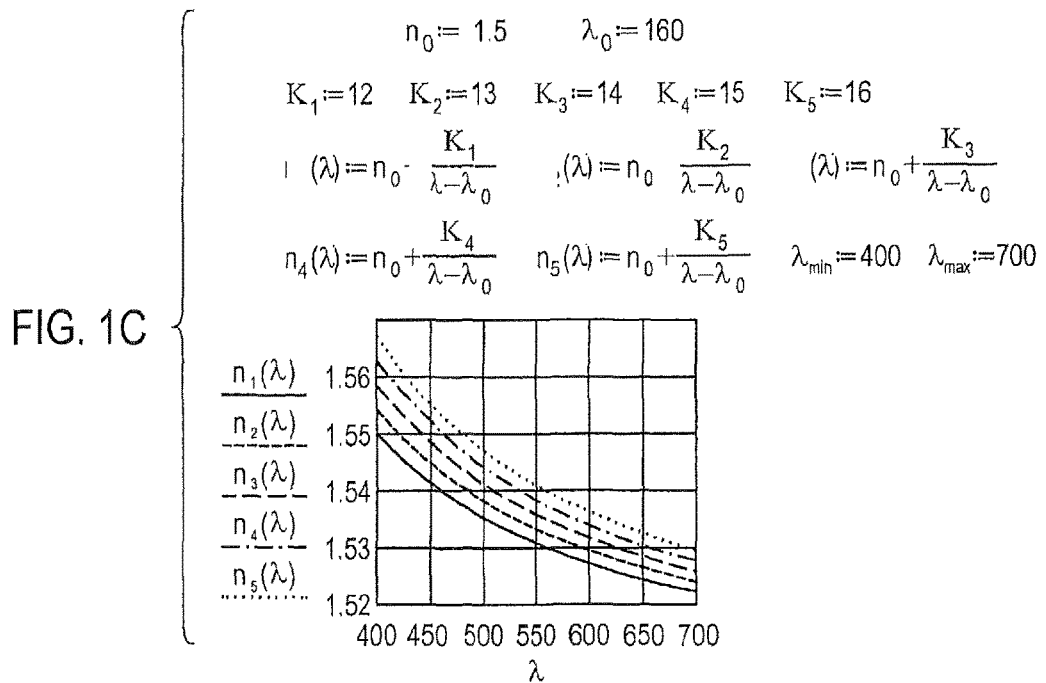
Figure 1D:
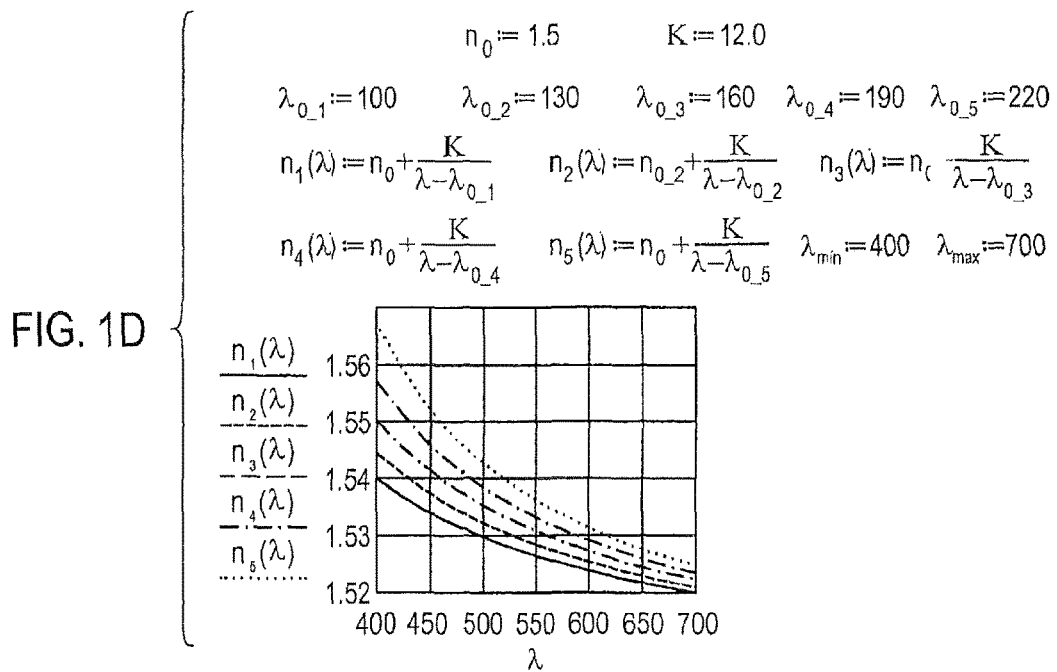

Referring to FIG. 1(a), there is depicted a curve of a glass dispersion function characterized by the Hartmann Dispersion Formula: $n(\lambda)=n_o+K/(\lambda-\lambda_o)$, where K and $\lambda_o$ are constants which are individual for each optical glass. Referring to FIG. 1(b), there are depicted curves of five glass dispersion functions characterized by the Hartmann Dispersion Formula where only the $n_o$ values vary. Referring to FIG. 1(c), there are depicted curves where only the K values of the Hartmann Dispersion Formula vary. Referring to FIG. 1(d), there are depicted curves where only the λo values of the Hartmann Dispersion Formula vary. FIG. 1(a) through 1(d) illustrate that for the optical glasses of a group of lenses, proper combinations for the $n_o$ and K values can be found to correct the chromatic aberrations of the group of optical lenses and that the $\lambda_o$ values of the glasses of such a group of lenses determine how much the chromatic aberrations of the group of lenses vary over the wavelength range for $\lambda_o$.

Figure 1E:
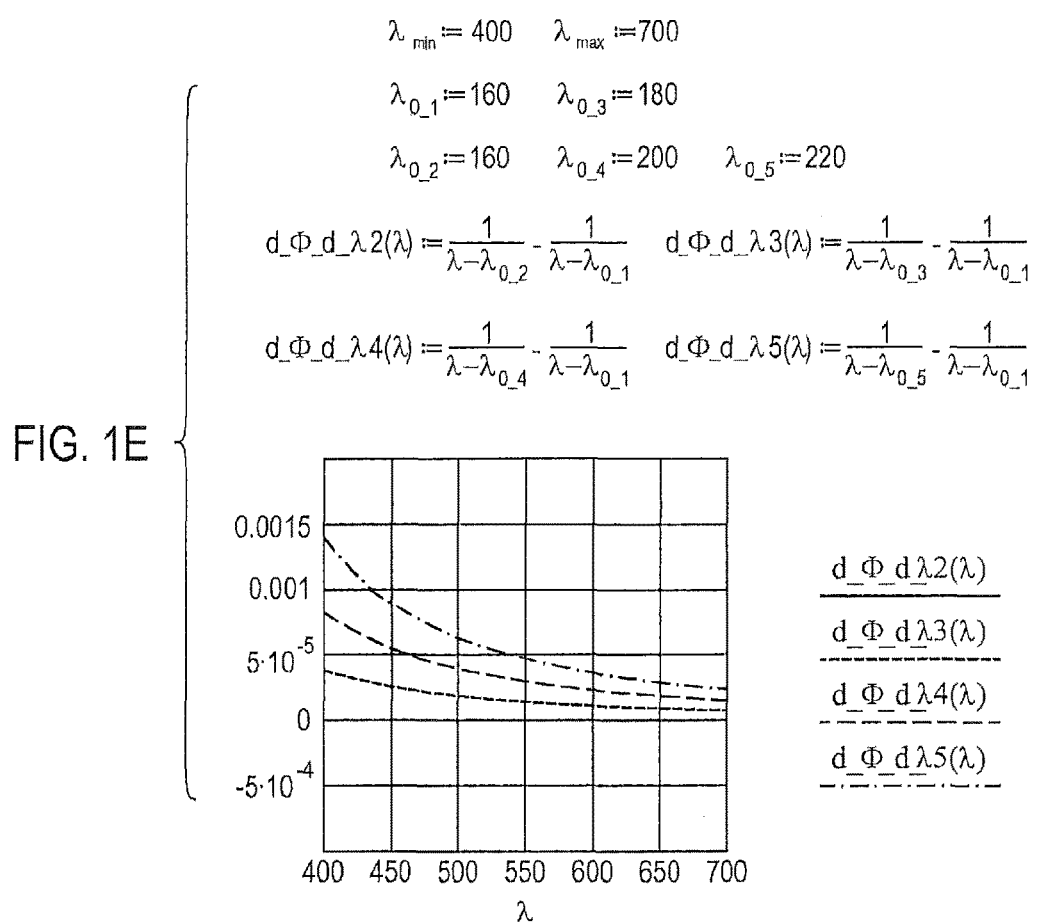

Referring to FIG. 1(e), there is depicted the variation of refractive power for different combinations of $\lambda_o$ values in an achromat. The variation of refractive power in an achromat does not change if both glasses of the lenses of the achromat have the same $\lambda_o$ value. The larger the difference of the $\lambda_o$ values, the larger the variation of the refractive power over the wavelength range $\lambda_o$. So, in accordance with the present invention, for each functional lens group, a fixed range for the selection of the $\lambda_o$ values has to be set based on the overall contribution of this lens group to the chromatic aberrations of the whole optical system.

Figure 2:
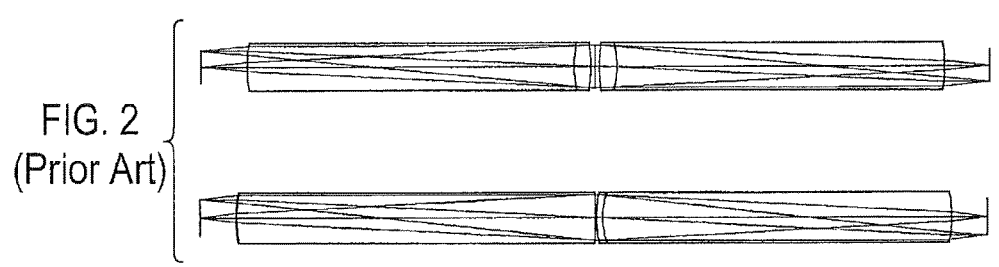
FIG. 2 depicts a prior art a symmetric relay system and a prior art asymmetric relay system.
Figure 3:
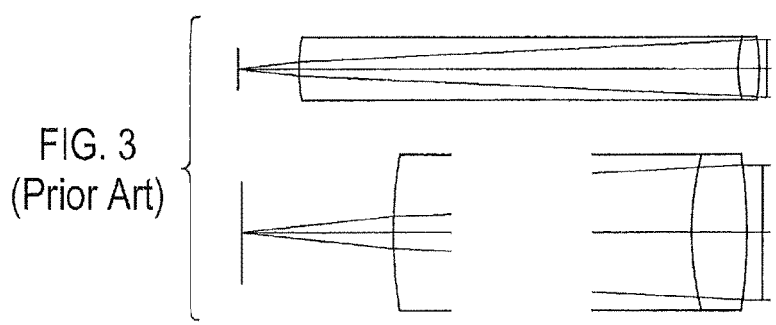
FIG. 3 depicts half of the symmetric relay system of FIG. 2 and a magnified view of an image side and an aperture side of the rod lens thereof.

Referring to FIG. 2, there is depicted a prior art symmetric relay system and a prior art asymmetric relay system. Referring to FIG. 3, there is depicted half of the symmetric relay system of FIG. 2 and a magnified view of an image side and an aperture side of the rod lens. It is shown that the diameter of the ray bundle coming from an axial image point is small at the image side and much larger on the aperture side. The lens elements on the aperture side of this rod lens contribute much more to the spherical aberration of the optical system than the lens elements on the image side of the rod lens. Therefore, according to the present invention, the range for the selection of the $\lambda_o$ values for the glasses on the aperture side of the rod lens must be much smaller than the range for the selection of the $\lambda_o$ values for the glasses on the image side.

Figures 4A, 4B:
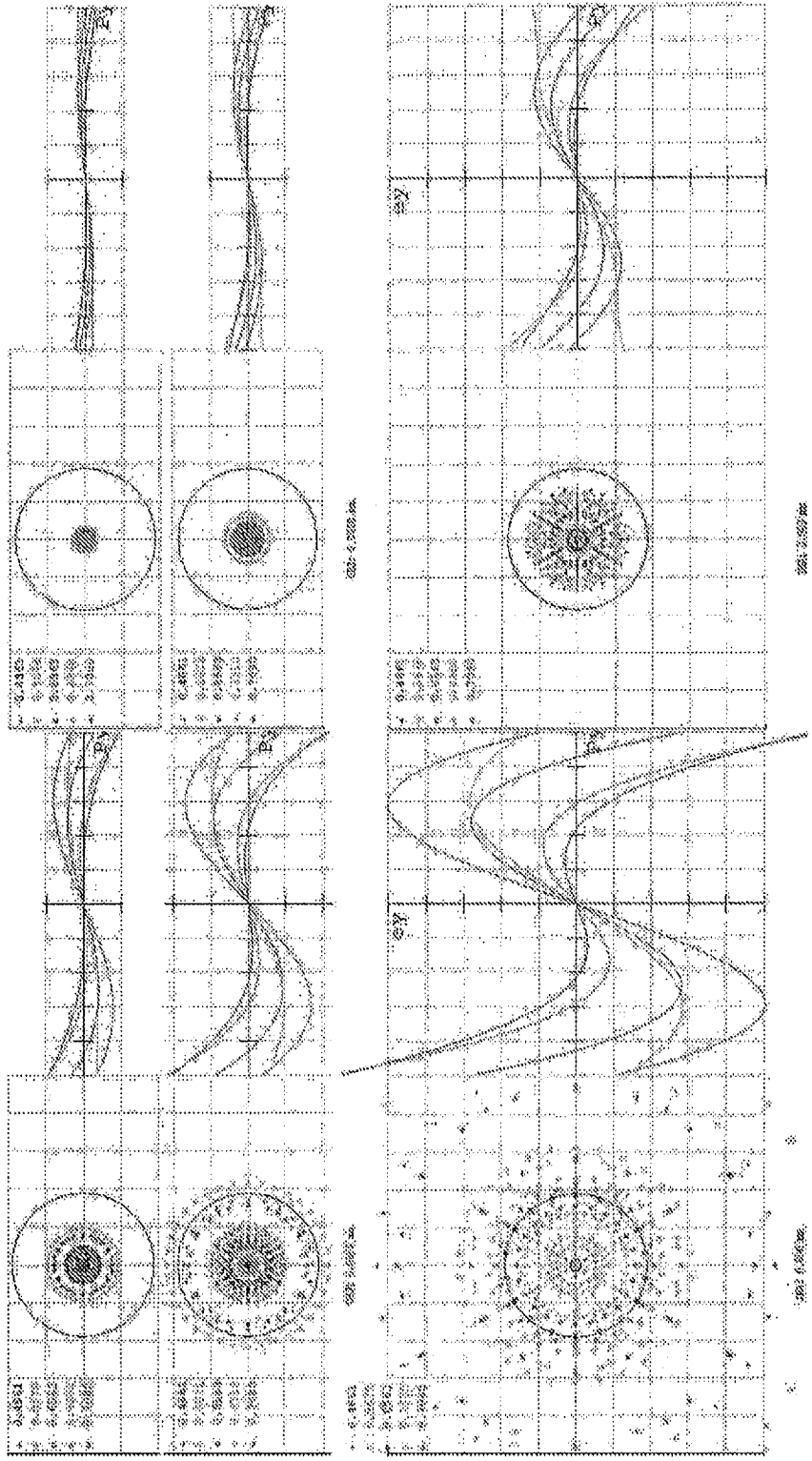
FIG. 4(*a*) graphically depicts the variation of aberrations for a large range of $\lambda_o$, values for a prior art optical system.

Referring to FIG. 4(a), there is graphically depicted the variation of aberrations for a large range of $\lambda_o$ values for the symmetrical relay system depicted in FIG. 2. On the right side of FIG. 4(a) are the aberration curves, and on the left side the spot diagrams. The black circles in the spot diagrams show the sizes of the airy disks representing the diffraction limits. It is shown that the spherical aberrations for one relay of this symmetric rod lens system exceed the diffraction limit. For three full relays, the spherical aberrations far exceed the diffraction limit of the optical system. In the top graphs are shown the spherical aberrations for five wavelengths of the prior art rod lens, which is half of a symmetric rod lens system. In the middle graph are the spherical aberrations for the same five wavelengths of both rod lenses of the symmetric rod lens system. The bottom shows the spherical aberrations for the five wavelengths of six rod lenses which are equal to three relays of the symmetrical rod lens system.

Referring to FIG. 4(b), there is graphically depicted the variation of aberrations for a small range of $\lambda_o$ values of an optical system in accordance with the present invention. On the right side of FIG. 4(b) are the aberration curves, and on the left side the spot diagrams. It is shown that the spherical aberrations for three complete relays of a symmetric rod lens system coincide with the diffraction limit if the $\lambda_o$ values of the glasses are selected from a small range for the $\lambda_o$ values according to the disclosed optical system.

Figure 5:
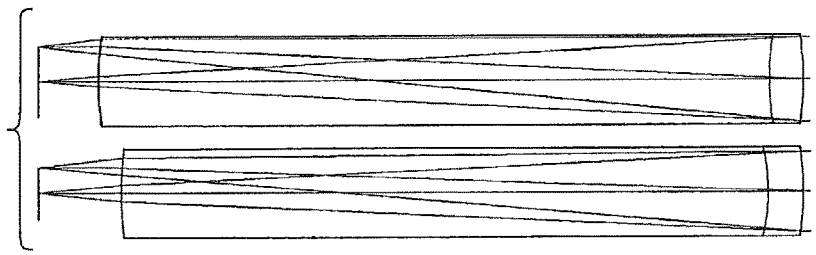
FIG. 5 depicts prior art rod lenses representing half of symmetric rod lens relay system with a single cap.
Figure 6:
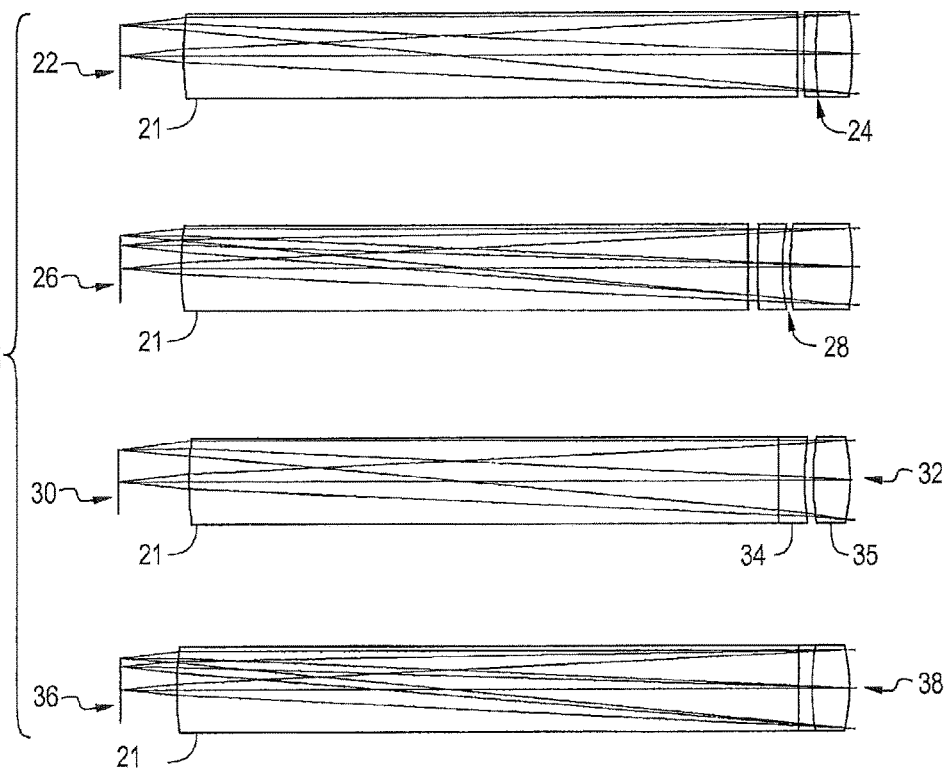
FIG. 6 depicts rod lenses representing half of symmetric rod lens relay system according to the present invention.

Referring to FIG. 5, there are depicted prior art rod lenses of symmetrical rod lens relay systems with a single cap. Referring to FIG. 6, there are depicted rod lenses 21 representing half symmetric rod lens relay systems according to the present invention. The first or top relay system 22 shows a rod lens system where the achromatic system is a separate achromat 24 and separated from rod lens 21 by an air gap. The second relay system 26 shows a rod lens system where the achromatic system is a split achromat 28 or so called Gaussian achromat where the achromat lenses are separated from one another and rod lens 21 by air gaps. The third relay system 30 shows a rod lens system where the achromatic system is a split achromat 32 with the flint lens 34 of the achromat cemented on the rod lens 21 and the positive lens 35 separated from the flint lens 34 by an air gap. The fourth or bottom relay system 36 shows a rod lens system where the achromatic system is an achromat 38 cemented on the rod lens 21. In each of the relay systems depicted in FIG. 6, the curvature of the lenses is spherical, while some of the glass air surfaces are aspherical surfaces. The $\lambda_o$ values of the glasses of these achromatic components in the relay systems are selected from a small range for the $\lambda_o$ values.

Figure 7:
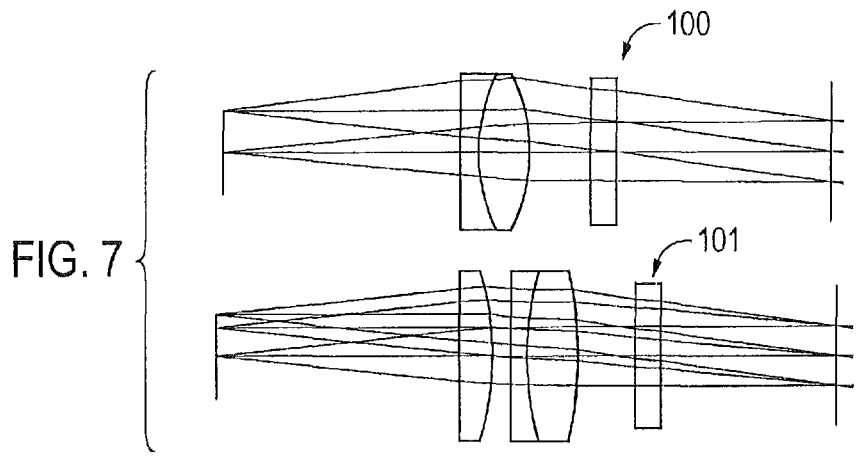
FIG. 7 depicts ocular lenses according the present invention with selection for $\lambda_o$.

Referring to FIG. 7, there are depicted ocular lens groups 100 and 101 according to the present invention with selection for $\lambda_o$. The $\lambda_o$ values of the glasses of these oculars are selected from a small range for the $\lambda_o$ values.

Figure 8A:
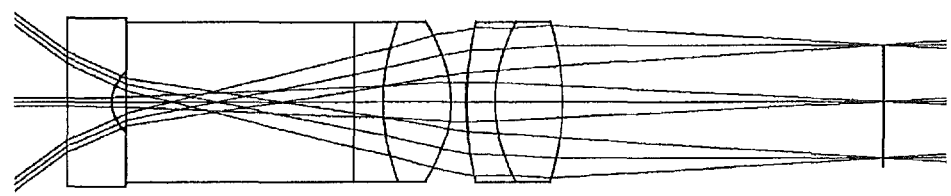
FIG. 8(*a*) depicts a prior art objective system for Hopkins rod lens systems.
Figure 8B:
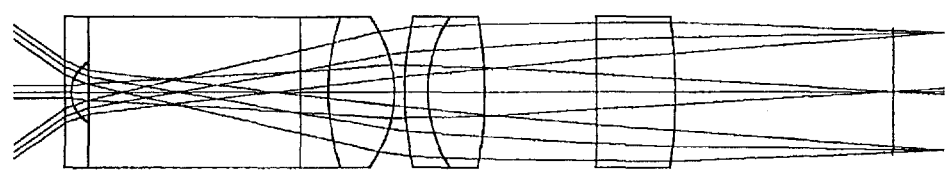
Figure 8C:
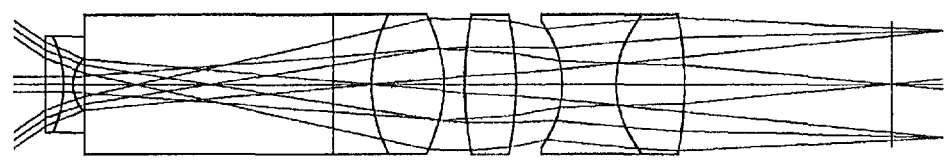

Referring to FIGS. 8(a) to 8(c), there are depicted different generations of state of the art objective systems for Hopkins rod lens systems. FIG. 8(a) depicts a prior art objective system for Hopkins rod lens systems. FIG. 8(b) depicts another prior art objective system for Hopkins rod lens systems. FIG. 8(c) depicts an advanced objective system for Hopkins rod lens systems.

Figure 9A:
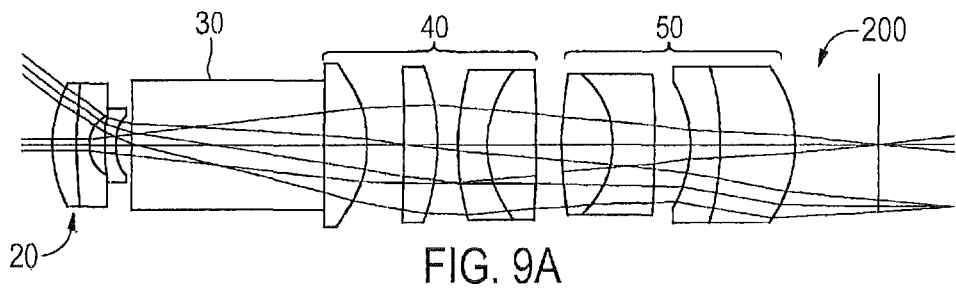
FIG. 9(*a*) depicts a first objective system for a rod lens system in accordance with the present invention.
Figure 9B:
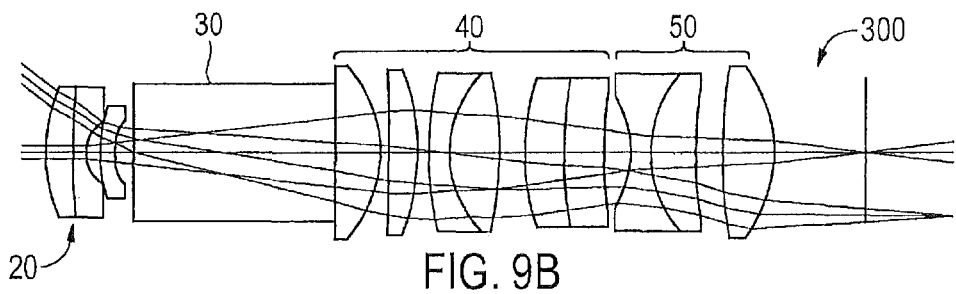
Figure 9C:
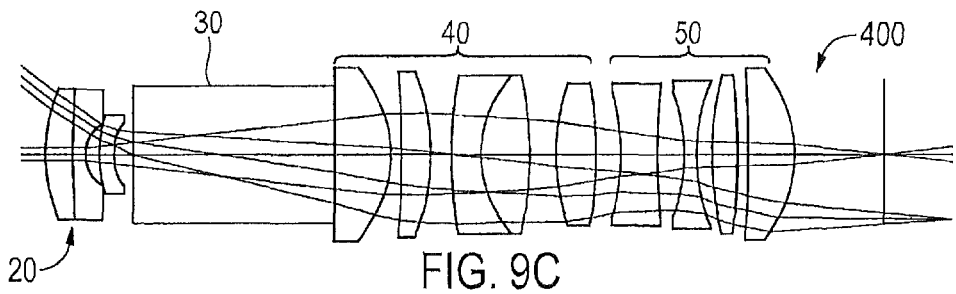
Figure 9D:
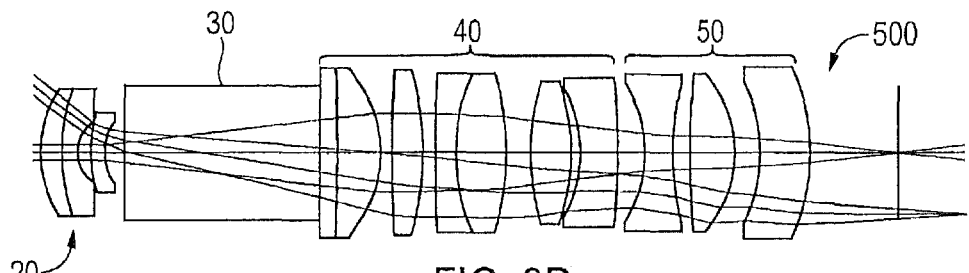
Figure 9E:
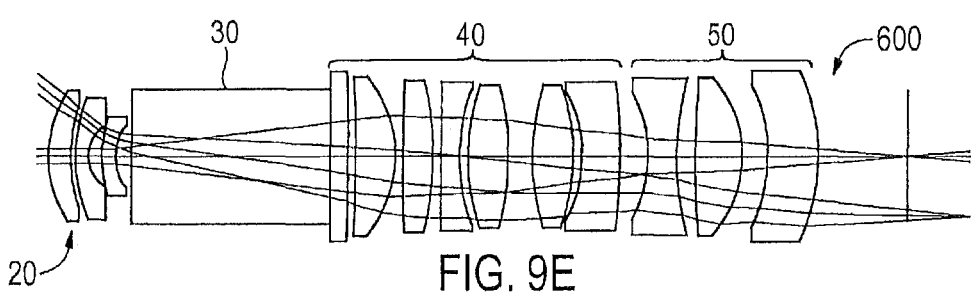

Referring to FIGS. 9(a) to 9(e), there are depicted typical variations of objective systems for rod lens systems according to the present invention. FIG. 9(a) depicts a first objective system 200 for rod lens systems in accordance with the present invention including eleven lenses in seven lens groups. FIG. 9(b) depicts a second objective system 300 for rod lens systems in accordance with the present invention including twelve lenses in eight lens groups. FIG. 9(c) depicts a third objective system 400 for rod lens systems in accordance with the present invention including twelve lenses in ten lens groups. FIG. 9(d) depicts a fourth objective system 500 for rod lens systems in accordance with the present invention including thirteen lenses in ten lens groups. FIG. 9(e) depicts a fifth objective system 600 for rod lens systems in accordance with the present invention. Each of the variations of the objective system has a negative lens group 20, a prism group 30, an objective lens group 40 and a field lens group 50, each lens group 20, 40, 50 containing three to five lenses. Prism block 30 is represented by a single glass rod as used in 0° objectives. For optical systems with deflected optical axes, prism block 30 is a state of the art prism block. For each lens group 20, 40, 50, a range for the $\lambda_o$ value of the glasses in this group is set or predetermined.

Figure 10A:
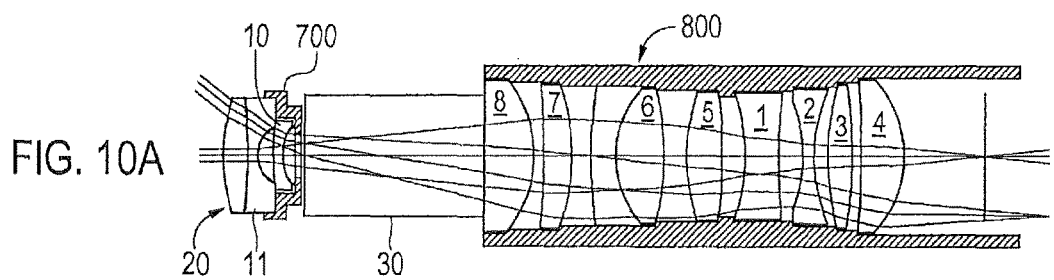
FIG. 10(*a*) depicts the objective system of FIG. 9(*c*) contained within a cartridge assembly in accordance with the optical system of the present invention.
FIG. 10(b) depicts a front lens group, an objective lens and field lens group and a cartridge assembly of the objective system of FIG. 10(a) with a prism block removed.
FIG. 10(c) depicts the objective lens group and cartridge assembly of the objective system of FIG. 10(a) without the field lens group.
FIG. 10(d) depicts the field lens group and cartridge assembly of the objective system of FIG. 10(a) without the objective lens group.
FIG. 10(e) depicts the cartridge assembly of FIG. 10(a) including a front lens group cartridge and a shared cartridge of the objective lens group and a field lens group without the lenses of the objective system.
Figure 10B:
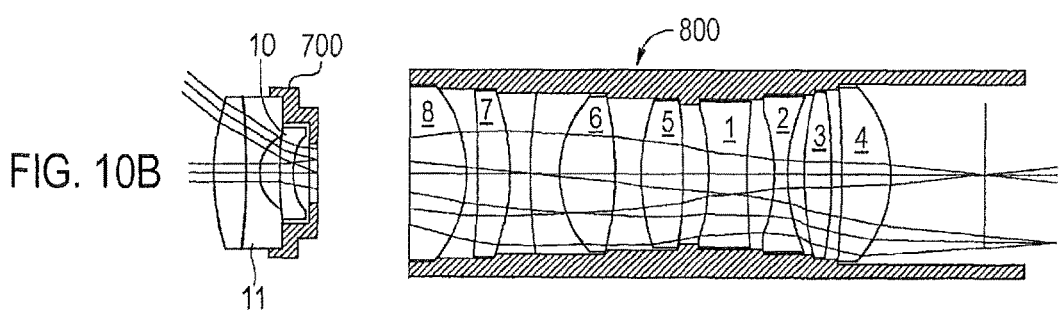
Figure 10C:
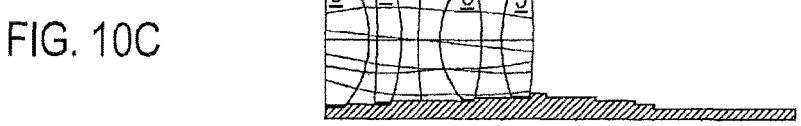
Figure 10D:
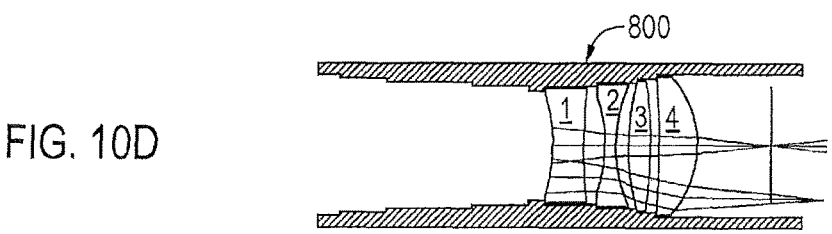
Figure 10E:
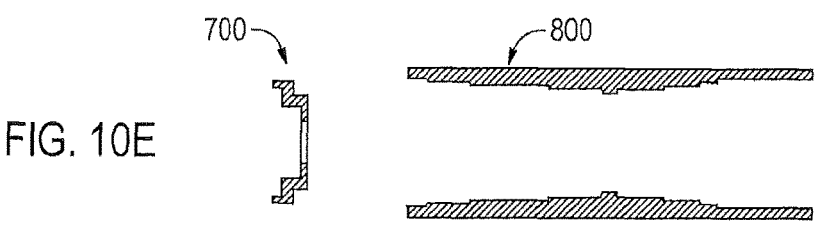

Referring to FIG. 10(a), there is depicted third objective system 400 assembled within a mechanical cartridge assembly consisting of a front cartridge 700 and a shared cartridge 800 holding the lenses of lens groups 20, 40, 50. As shown, field lens group 50 includes lenses, 1, 2, 3 and 4. Objective lens group 40 includes lenses 5, 7 and 8 and achromat 6. Negative lens group 20 includes lenses 10 and 11. FIG. 10(b) depicts front lens group 20 of the rod lens system of FIG. 10(a) within front cartridge 700 and objective lens and field lens groups 30, 40 in shared cartridge 800 without prism group 30. FIG. 10(c) shows the objective lens group alone in the shared cartridge, and FIG. 10(d) shows the field lens group alone in the shared cartridge. FIG. 10(e) shows front cartridge 700 and the shared cartridge 800 without the lenses.

Figure 11:
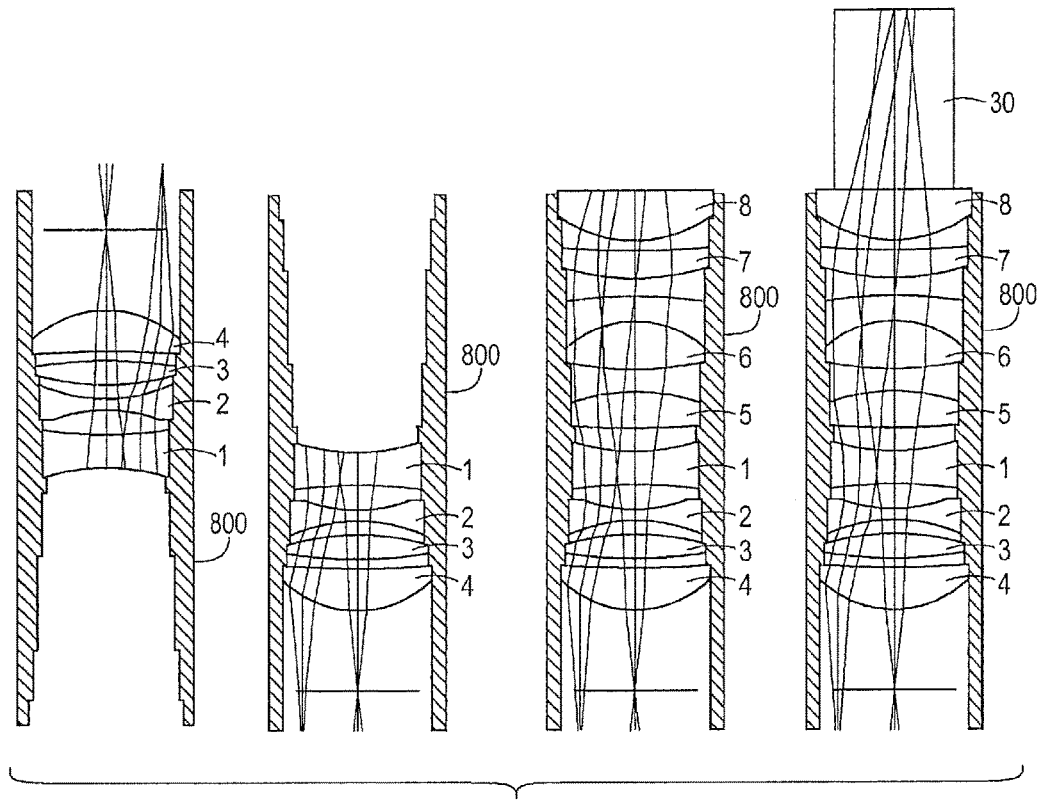
FIG. 11 depicts a method of assembling the objective lens group and field lens group and prism block of the objective system of FIG. 10(a) within a shared cartridge in accordance with the present invention.

Referring to FIG. 11, there is depicted a method of assembling objective lens group 40, field lens group 50 and prism block 30 within shared cartridge 800 of FIG. 10(a). In particular, FIG. 11 shows how the design of shared cartridge 800 allows field lens group 50 and objective lens group 40 to be aligned relative to one another and relative to prism group 30, lens by lens. On the left image of FIG. 11, the field lenses 1, 2, 3 and 4 are aligned and fixed in place one lens at a time. Then, shared cartridge 800 is turned upside down as shown in FIG. 11. Then the objective lenses 5, 6, 7 and 8 are aligned and fixed in place one lens at a time. In the last step, the prism block 30 or glass block 30 is aligned at the top of shared cartridge 800 containing the lenses 1 to 8.

Figure 12A:
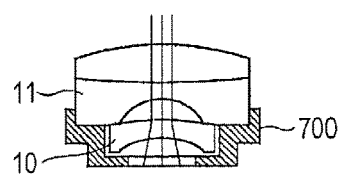
FIG. 12(a) depicts a method of assembling the negative lenses of the objective system of FIG. 10(a) within a front cartridge in accordance with the present invention.
Figure 12B:
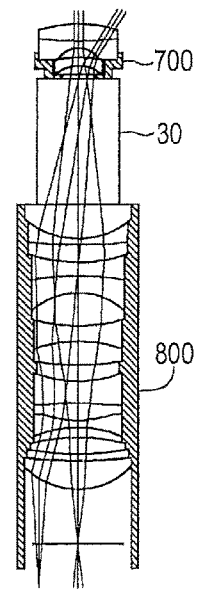
FIG. 12(b) depicts a method assembling the front lens group cartridge on the prism block sitting on top of the objective assembly of FIG. 10(a).

Referring to FIG. 12(a), there is depicted a method of assembling negative lenses 10 and 11 within front cartridge 700. In particular, FIG. 12(a) shows how the design of the front cartridge allows the lenses 10 and 11 of the front lens group to be aligned relative to one another and relative to the front cartridge lens by lens. Referring to FIG. 12(b), there is depicted a method assembling the front cartridge with the shared cartridge. As shown, front cartridge 700 with assembled lenses is aligned on top of prism block 30 or glass block 30 of the first cartridge.

EXAMPLE

Figure 15:
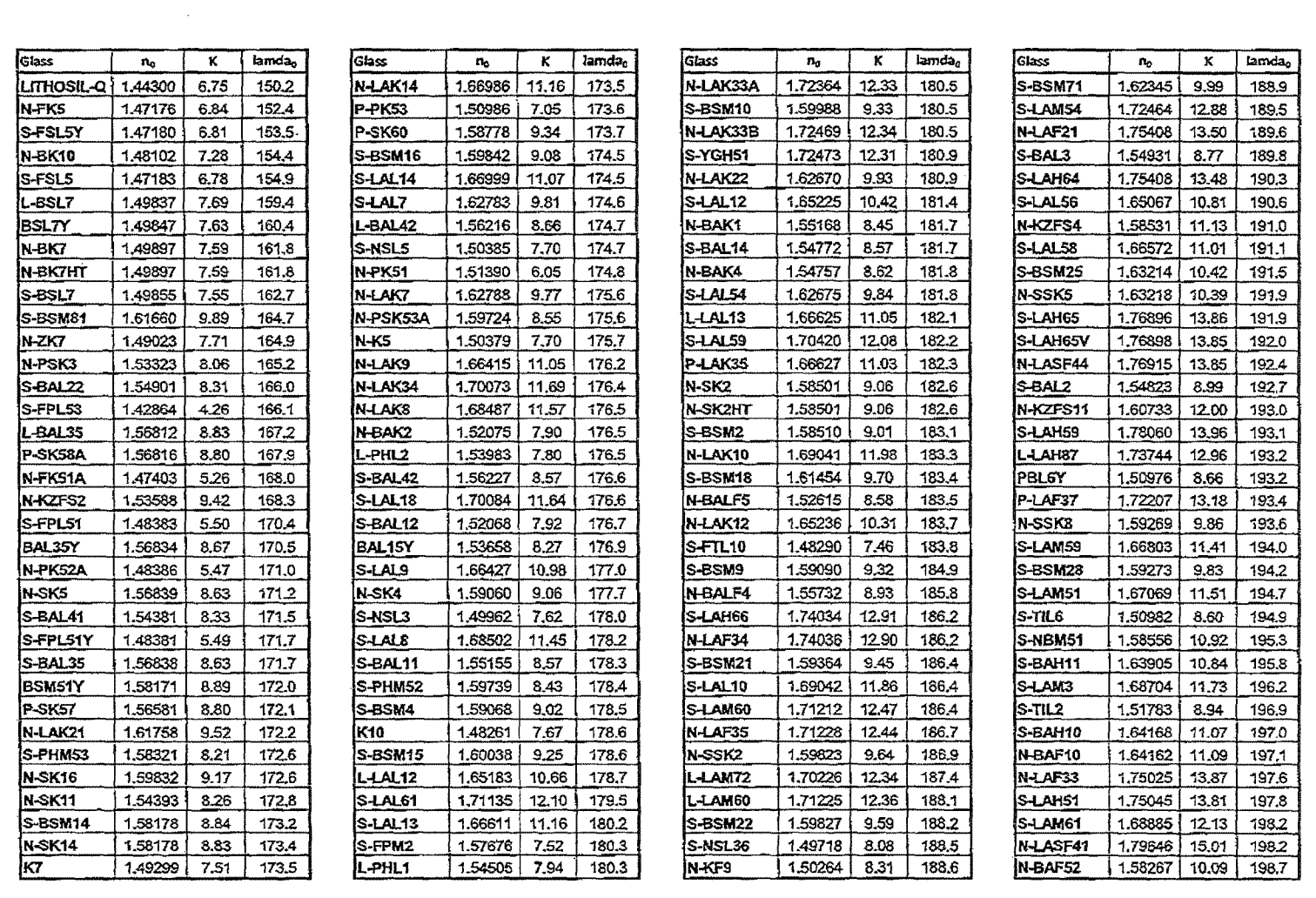

The various glass types that are available for use to produce lenses for optical assemblies are well known in the art, as are the refractive indices and Hartmann constants $n_o$, $\lambda o$ and K of the glasses. (Lee, H. W., "*The Hartmann Formula for the Dispersion of Glass*," Transactions for the optical Society, Vol. 28, No. 3 (1927)). In particular, glass manufacturers regularly publish catalogs containing tables listing refractive indices for their glasses. FIG. 13 depicts a table displaying refractive indices aggregated from different manufacturer catalogs for different glasses for three wavelengths where each of $n_c$, $n_d$ and $n_f$ represent the respective refractive indices for the glasses for a particular wavelength. In possession of the refractive indices of the glasses, the Hartmann constants $n_o$, $\lambda o$ and K can be calculated from a derivation of the Hartman formula. FIG. 14 shows the derivation of the Hartmann formula for calculating the Hartman constants from three wavelengths. Utilizing PTC's Mathcad computer program and the Hartmann derivation displayed in FIG. 14, Hartmann constants $n_o$, $\lambda o$ and K for glasses can be quickly calculated and output. FIG. 15 depicts a table displaying the Hartman constants $n_o$, $\lambda o$ and K for the glasses represented in FIG. 13. FIG. 16 depicts an optical assembly in accordance with the present invention assembled from the glasses represented in FIG. 13 and utilizing the λo values displayed in FIG. 15.

As will be apparent to one skilled in the art, various modifications can be made within the scope of the aforesaid description. Such modifications being within the ability of one skilled in the art form a part of the present invention and are embraced by the claims below.

It is claimed:

1. An optical system for an endoscope comprising:
from an object side of the optical system, an objective assembly including a first lens group for creating a first image, a symmetric relay assembly including a second lens group for transmitting the first image to a proximal end of the endoscope and an ocular lens assembly including a third lens group for observing the relayed first image, the first lens group including from the object side, a negative refractive power lens group, a prism member, an objective lens group and a field lens group,
wherein each lens of the negative refractive power lens group and the prism member exhibits a $\lambda_o$ value within a first range of 25 nm or less, each lens of the objective lens group exhibits a $\lambda_o$ value within a second range of 15 nm or less, each lens of the field lens group exhibits a $\lambda_o$ value within a third range of 25 nm or less, each lens of the second lens group exhibits a $\lambda_o$ value within a fourth range of 15 nm or less, and each lens of the third lens group exhibits a $\lambda_o$ value within a fifth range of 30 nm or less, where the $\lambda_o$ value is expressed with the following formula:

$$n(\lambda)=n_o+K/(\lambda-\lambda_o)$$

where λ denotes a wavelength and $n_o$, K and $\lambda_o$ are a set of empirical constants varying for each lens glass type, and
wherein the first range is the difference between a largest λo value and a smallest λo value represented by the lenses of the negative refractive power lens group and the prism member, the second range is the difference between a largest λo value and a smallest λo value represented by the lenses of the objective lens group, the third range is the difference between a largest λo value and a smallest λo value represented by the lenses of the field lens group, the fourth range is the difference between a largest λo value and a smallest λo value represented by the lenses of the second lens group, and the fifth range is the difference between a largest λo value and a smallest λo value represented by the lenses of the third lens group.

2. The optical system according to claim 1 wherein the negative refractive power lens group, the objective lens group and the field lens group each contains three to five lenses.

3. The optical system according to claim 1 wherein objective lens group and the field lens group are assembled and optically aligned within a first housing.

4. The optical system according to claim 3 wherein the negative refractive power lens group is assembled and optically aligned within a second housing.

5. The optical system according to claim 4 wherein the negative refractive power lens group is optically aligned with the objective lens group and the field lens group.

6. The optical system according to claim 1 wherein the symmetric relay assembly includes an achromatic lens member having an achromat separated from a rod lens.

7. The optical system according to claim 1 wherein the symmetric relay assembly includes an achromatic lens member having lenses that are separated from one another by an air gap.

8. The optical system according to claim 1 wherein the symmetric relay assembly includes an achromatic lens member having a lens with an aspherical surface.

9. The optical system according to claim 1 wherein the negative refractive power lens group is assembled and optically aligned within housing and optically aligned at the object side of the prism member.

10. The optical system according to claim 1 wherein each lens of the second lens group that is located on an aperture side of the symmetric relay assembly exhibits a $\lambda_o$ value within a range of 6 nm or less, wherein the range of 6 nm or less is the difference between a largest λo value and a smallest λo value represented by the lenses of the second lens group that are located on the aperture side of the symmetric relay assembly.

11. An optical system for an endoscope comprising:
an objective assembly having a first lens group including a negative refractive power lens group, a prism member, an objective lens group and a field lens group, wherein each lens of the negative refractive power lens group and the prism group exhibits a $\lambda_o$ value within a first range of 25 nm or less, each lens of the objective lens group exhibits a $\lambda_o$ value within a second range of 15 nm or less, and each lens of the field lens group exhibits a $\lambda_o$ value within a third range of 25 nm or less, where the $\lambda_o$ value is expressed with the following formula:

$$n(\lambda)=n_o+K/(\lambda-\lambda_o)$$

where λ denotes a wavelength and $n_o$, K and $\lambda_o$ are a set of empirical constants varying for each lens glass type,
a relay assembly including a second lens group, and
an ocular lens assembly including a third lens group,
wherein the negative refractive power lens group, the objective lens group and the field lens group each contains at least three lenses, and
wherein the first range is the difference between a largest λo value and a smallest λo value represented by the lenses of the negative refractive power lens group and the prism member, the second range is the difference between a largest λo value and a smallest λo value represented by the lenses of the objective lens group, and the third range is the difference between a largest λo value and a smallest λo value represented by the lenses of the field lens group.

12. The optical system according to claim 11 wherein each lens of the second lens group exhibits a $\lambda_o$ value within a fourth range of 15 nm or less, the fourth range being the difference between a largest λo value and a smallest λo value represented by the lenses of the second lens group.

13. The optical system according to claim 11 wherein each lens of the third lens group exhibits a $\lambda_o$ value within a fifth range of 30 nm or less, and the fifth range being the difference between a largest λo value and a smallest λo value represented by the lenses of the third lens group.

14. The optical system according to claim 11 wherein the objective lens group and the field lens group are assembled and optically aligned within a first housing, the negative refractive power lens group is assembled and optically aligned within a second housing and the negative refractive power lens group is optically aligned with the objective lens group and the field lens group.

15. The optical system according to claim 11 wherein the relay assembly includes an achromatic lens member having an achromat separated from a center rod lens.

16. The optical system according to claim 15 wherein the achromatic lens member includes lenses that are separated from one another by an air gap.

17. The optical system according to claim 11 wherein the relay assembly includes an achromatic lens member having a lens with an aspherical surface.

18. The optical system according to claim 11 wherein each lens of the second lens group that is located on an aperture side of the relay assembly exhibits a $\lambda_o$ value within range of 6 nm or less, wherein the range of 6 nm or less is the difference between a largest $\lambda$o value and a smallest $\lambda$o value represented by the lenses of the second lens group that are located on the aperture side of the symmetric relay assembly.

19. A method of making an optical system for an endoscope comprising:
  selecting at least three lenses and a prism member that each exhibit a $\lambda_o$ value within a first range and arranging the at least three lenses into a negative refractive power lens assembly, the first range being the difference between a largest $\lambda$o value and a smallest $\lambda$o value represented by the at least three lenses of the negative refractive power lens assembly and the prism member,
  selecting at least three lenses that each exhibit a $\lambda_o$ value within a second range and arranging the at least three lenses into an objective lens assembly, the second range being the difference between a largest $\lambda$o value and a smallest $\lambda$o value represented by the at least three lenses of the objective lens assembly,
  selecting at least three lenses that each exhibit a $\lambda_o$ value within a third range and arranging the at least three lenses into a field lens assembly, the third range being the difference between a largest $\lambda$o value and a smallest $\lambda$o value represented by the at least three lenses of the field lens assembly,
  selecting a plurality of lenses that each exhibit a $\lambda_o$ value within a fourth range and arranging the plurality of lenses into a symmetric relay assembly, the fourth range being the difference between a largest $\lambda$o value and a smallest $\lambda$o value represented by the plurality of lenses of the relay assembly, and
  selecting a plurality of lenses that each exhibit a $\lambda_o$ value within a fifth range and arranging the plurality of lenses into an ocular lens assembly, the fifth range being the difference between a largest $\lambda$o value and a smallest $\lambda$o value represented by the plurality of lenses of the ocular lens assembly, and
  optically aligning the negative refractive power lens assembly, the prism member, the objective lens assembly, the field lens assembly, the symmetric relay assembly and the ocular lens assembly,
  wherein the $\lambda_o$ value is expressed with the following formula:

$$n(\lambda)=n_o+K/(\lambda-\lambda_o)$$

where $\lambda$ denotes a wavelength and $n_o$, K and $\lambda_o$ are a set of empirical constants varying for each lens glass type.

20. The method according to claim 19 wherein the first range is 25 nm or less.

21. The method according to claim 19 wherein the second range is 15 nm or less.

22. The method according to claim 19 wherein third range is 25 nm or less.

23. The method according to claim 19 wherein the fourth range is 15 nm or less.

24. The method according to claim 19 wherein the fifth range is 30 nm or less.

25. The method according to claim 19 wherein the first range is 25 nm or less, the second range is 15 nm or less and the third range is 25 nm or less.

26. The method according to claim 25 wherein the fourth range is 15 nm or less.

27. The method according to claim 19 wherein the fourth range is smaller than the third range.

28. The method according to claim 19 wherein the fourth range is smaller than the fifth range.

29. The method according to claim 27 wherein the fourth range is smaller than the fifth range.

* * * * *